(12) United States Patent
Hung et al.

(10) Patent No.: US 9,388,374 B2
(45) Date of Patent: Jul. 12, 2016

(54) MICROFLUIDIC CELL CULTURE SYSTEMS

(75) Inventors: Paul J. Hung, Berkeley, CA (US);
Philip J. Lee, Alameda, CA (US)

(73) Assignee: EMD Millipore Corporation, Billerica, MA (US)

( * ) Notice: Subject to any disclaimer, the term of this patent is extended or adjusted under 35 U.S.C. 154(b) by 0 days.

(21) Appl. No.: 13/011,857

(22) Filed: Jan. 21, 2011

(65) Prior Publication Data
US 2012/0003732 A1    Jan. 5, 2012

Related U.S. Application Data

(60) Provisional application No. 61/367,371, filed on Jul. 23, 2010, provisional application No. 61/297,278, filed on Jan. 21, 2010.

(51) Int. Cl.
*C12M 1/00* (2006.01)
*C12M 3/00* (2006.01)
*C12M 3/06* (2006.01)

(52) U.S. Cl.
CPC ............... *C12M 23/16* (2013.01); *C12M 21/08* (2013.01)

(58) Field of Classification Search
CPC .............................. C12M 23/16; C12M 29/10
USPC ...................................................... 435/289.1
See application file for complete search history.

(56) References Cited

U.S. PATENT DOCUMENTS

| 4,055,613 A | 10/1977 | Kapral |
| 4,661,455 A | 4/1987 | Hubbard |
| 4,734,373 A | 3/1988 | Bartal |
| 4,748,124 A | 5/1988 | Vogler |
| 5,079,168 A | 1/1992 | Amiot |

(Continued)

FOREIGN PATENT DOCUMENTS

| DE | 19948087 | 5/2001 |
| DE | 19948087 A1 | 5/2001 |

(Continued)

OTHER PUBLICATIONS

Lee et al. (2007) "Microfluidic System for Automated Cell-Based Assays." JALA. 1-19.*

(Continued)

*Primary Examiner* — Michael Hobbs
*Assistant Examiner* — Liban Hassan
(74) *Attorney, Agent, or Firm* — Nields, Lemack & Frame, LLC

(57) ABSTRACT

In one embodiment, a microfluidic structure comprises a culture chamber having an object flow inlet disposed between a pair of object flow outlets. A flow-around channel provides fluidic mass transport to the culture chamber through a perfusion barrier disposed opposite from the object flow inlet and object flow outlets. The perfusion barrier surrounds the culture chamber, defines an opposite wall of the culture chamber, and prevents cell passage into the flow around-channel. The perfusion barrier creates a low fluidic resistance path within the culture chamber, such that a flow of cells entering the culture chamber from the object flow inlet encounters a flow of media passing through the perfusion barrier. This causes the cells to take an approximately 180 degree turn and exit the culture chamber via the object flow outlets. The low fluidic resistance path allows the cells to settle onto the chamber floor without needing any physical barrier.

16 Claims, 35 Drawing Sheets

(56) References Cited

U.S. PATENT DOCUMENTS

| | | |
|---|---|---|
| 5,153,131 A | 10/1992 | Wolf et al. |
| 5,310,676 A | 5/1994 | Johansson et al. |
| 5,330,908 A | 7/1994 | Spaulding |
| 5,376,252 A | 12/1994 | Ekstrom et al. |
| 5,416,022 A | 5/1995 | Amiot |
| 5,424,209 A | 6/1995 | Kearney |
| 5,437,998 A | 8/1995 | Schwarz et al. |
| 5,451,524 A | 9/1995 | Coble et al. |
| 5,462,874 A | 10/1995 | Wolf et al. |
| 5,565,353 A | 10/1996 | Klebe et al. |
| 5,589,112 A | 12/1996 | Spaulding |
| 5,593,814 A | 1/1997 | Matsuda et al. |
| 5,602,028 A | 2/1997 | Minchinton |
| 5,627,070 A | 5/1997 | Gruenberg |
| 5,637,469 A | 6/1997 | Wilding et al. |
| 5,641,644 A | 6/1997 | Klebe |
| 5,658,797 A | 8/1997 | Bader |
| 5,686,301 A | 11/1997 | Falkenberg et al. |
| 5,686,304 A | 11/1997 | Codner |
| 5,693,537 A | 12/1997 | Wilson et al. |
| 5,702,941 A | 12/1997 | Schwarz |
| 5,714,384 A | 2/1998 | Wilson et al. |
| 5,763,261 A | 6/1998 | Gruenberg |
| 5,763,275 A | 6/1998 | Nagels et al. |
| 5,763,279 A | 6/1998 | Schwarz et al. |
| 5,786,215 A | 7/1998 | Brown et al. |
| 5,793,440 A | 8/1998 | Nakasaka et al. |
| 5,801,054 A | 9/1998 | Kiel et al. |
| 5,866,345 A | 2/1999 | Wilding et al. |
| 5,882,918 A | 3/1999 | Goffe |
| 5,900,361 A | 5/1999 | Klebe |
| 5,912,177 A | 6/1999 | Turner et al. |
| 5,924,583 A | 7/1999 | Stevens et al. |
| 5,932,315 A | 8/1999 | Lum et al. |
| 5,942,443 A | 8/1999 | Parce et al. |
| 6,039,897 A | 3/2000 | Lochhead et al. |
| 6,048,498 A | 4/2000 | Kennedy |
| 6,096,532 A | 8/2000 | Armstrong et al. |
| 6,107,085 A | 8/2000 | Coughlin et al. |
| 6,153,073 A | 11/2000 | Dubrow et al. |
| 6,190,913 B1 | 2/2001 | Singh |
| 6,197,575 B1 | 3/2001 | Griffith et al. |
| 6,228,635 B1 | 5/2001 | Armstrong et al. |
| 6,238,908 B1 | 5/2001 | Armstrong et al. |
| 6,251,343 B1 | 6/2001 | Dubrow et al. |
| 6,274,337 B1 | 8/2001 | Parce et al. |
| 6,277,642 B1 | 8/2001 | Mentzen et al. |
| 6,297,046 B1 | 10/2001 | Smith et al. |
| 6,323,022 B1 | 11/2001 | Change et al. |
| 6,326,211 B1 | 12/2001 | Anderson et al. |
| 6,403,369 B1 | 6/2002 | Wood |
| 6,410,309 B1 | 6/2002 | Barbera-Guillem et al. |
| 6,455,310 B1 | 9/2002 | Barbera-Guillem |
| 6,465,243 B2 | 10/2002 | Okada et al. |
| 6,468,792 B1 | 10/2002 | Bader |
| 6,481,648 B1 | 11/2002 | Zimmermann |
| 6,495,104 B1 | 12/2002 | Unno et al. |
| 6,518,035 B1 | 2/2003 | Ashby et al. |
| 6,534,013 B1 | 3/2003 | Kennedy |
| 6,548,263 B1 | 4/2003 | Kapur et al. |
| 6,551,841 B1 | 4/2003 | Wilding et al. |
| 6,555,365 B2 | 4/2003 | Barbera-Guillem et al. |
| 6,562,616 B1 | 5/2003 | Toner et al. |
| 6,569,675 B2 | 5/2003 | Wall et al. |
| 6,576,458 B1 | 6/2003 | Sarem et al. |
| 6,585,744 B1 | 7/2003 | Griffith |
| 6,585,939 B1 | 7/2003 | Daprich |
| 6,593,136 B1 | 7/2003 | Geiss |
| 6,637,463 B1 * | 10/2003 | Lei et al. ................ 137/803 |
| 6,648,015 B1 | 11/2003 | Chow |
| 6,653,124 B1 | 11/2003 | Freeman |
| 6,673,595 B2 | 1/2004 | Barbera-Guillem |
| 6,756,019 B1 | 6/2004 | Dubrow et al. |
| 6,759,245 B1 | 7/2004 | Toner et al. |
| 6,794,184 B1 | 9/2004 | Mohr et al. |
| 6,811,752 B2 | 11/2004 | Barbera-Guillem |
| 6,821,772 B2 | 11/2004 | Barbera-Guillem et al. |
| 6,846,668 B1 | 1/2005 | Garman et al. |
| 6,857,449 B1 | 2/2005 | Chow |
| 6,908,767 B2 | 6/2005 | Bader |
| 6,915,679 B2 | 7/2005 | Chien et al. |
| 6,969,166 B2 | 11/2005 | Clark et al. |
| 7,005,292 B2 | 2/2006 | Wilding et al. |
| 7,018,830 B2 | 3/2006 | Wilding et al. |
| 7,022,518 B1 | 4/2006 | Feye |
| 7,067,263 B2 | 6/2006 | Parce et al. |
| 7,141,386 B2 | 11/2006 | Dunfield et al. |
| 7,155,344 B1 | 12/2006 | Parce et al. |
| 7,160,687 B1 | 1/2007 | Kapur et al. |
| 7,171,983 B2 | 2/2007 | Chien et al. |
| 7,192,769 B2 | 3/2007 | Pykett et al. |
| 7,223,371 B2 | 5/2007 | Hayenga et al. |
| 7,343,248 B2 | 3/2008 | Parce et al. |
| 7,745,209 B2 | 6/2010 | Martin et al. |
| 7,919,319 B2 | 4/2011 | Jervis et al. |
| 8,257,964 B2 | 9/2012 | Hung et al. |
| 8,673,625 B2 | 3/2014 | Hung et al. |
| 8,709,790 B2 | 4/2014 | Hung et al. |
| 9,206,384 B2 | 12/2015 | Lee et al. |
| 2002/0039785 A1 | 4/2002 | Schroeder et al. |
| 2002/0108860 A1 | 8/2002 | Staats |
| 2002/0110905 A1 | 8/2002 | Barbera-Guillem et al. |
| 2002/0177221 A1 | 11/2002 | Nishiguchi et al. |
| 2003/0008388 A1 | 1/2003 | Barbera-Guillem et al. |
| 2003/0008389 A1 | 1/2003 | Carll |
| 2003/0030184 A1 | 2/2003 | Kim |
| 2003/0040104 A1 | 2/2003 | Barbera-Guillem |
| 2003/0124623 A1 | 7/2003 | Yager et al. |
| 2003/0143727 A1 | 7/2003 | Chang |
| 2003/0156992 A1 | 8/2003 | Anderson et al. |
| 2003/0211012 A1 | 11/2003 | Bergstrom |
| 2004/0029266 A1 | 2/2004 | Barbera-Guillem |
| 2004/0043481 A1 | 3/2004 | Wilson |
| 2004/0072278 A1 | 4/2004 | Chou et al. |
| 2004/0096960 A1 | 5/2004 | Mehta et al. |
| 2004/0132175 A1 | 7/2004 | Vetillard et al. |
| 2004/0202579 A1 | 10/2004 | Larsson |
| 2004/0229349 A1 | 11/2004 | Daridon |
| 2004/0238484 A1 | 12/2004 | Le Pioufle et al. |
| 2005/0009179 A1 | 1/2005 | Gemmiti et al. |
| 2005/0019213 A1 * | 1/2005 | Kechagia et al. ............... 422/57 |
| 2005/0032208 A1 | 2/2005 | Oh et al. |
| 2005/0072946 A1 | 4/2005 | Studer et al. |
| 2005/0101009 A1 | 5/2005 | Wilson et al. |
| 2005/0106717 A1 | 5/2005 | Wilson et al. |
| 2005/0169962 A1 | 8/2005 | Bhatia et al. |
| 2005/0214173 A1 | 9/2005 | Facer et al. |
| 2005/0221373 A1 | 10/2005 | Enzelberger et al. |
| 2005/0260745 A1 | 11/2005 | Domansky et al. |
| 2005/0266582 A1 | 12/2005 | Modlin et al. |
| 2006/0003436 A1 | 1/2006 | DiMilla et al. |
| 2006/0031955 A1 | 2/2006 | West et al. |
| 2006/0112438 A1 | 5/2006 | West et al. |
| 2006/0121606 A1 | 6/2006 | Ito et al. |
| 2006/0136182 A1 | 6/2006 | Vacanti et al. |
| 2006/0141617 A1 | 6/2006 | Desai et al. |
| 2006/0154361 A1 * | 7/2006 | Wikswo et al. ............ 435/289.1 |
| 2006/0166354 A1 | 7/2006 | Wikswo et al. |
| 2006/0199260 A1 * | 9/2006 | Zhang et al. ............... 435/293.1 |
| 2007/0026516 A1 | 2/2007 | Martin et al. |
| 2007/0084706 A1 | 4/2007 | Takayama et al. |
| 2007/0090166 A1 | 4/2007 | Takayama et al. |
| 2007/0122314 A1 * | 5/2007 | Strand et al. ................... 422/100 |
| 2007/0128715 A1 * | 6/2007 | Vukasinovic et al. ...... 435/303.1 |
| 2007/0264705 A1 | 11/2007 | Dodgson |
| 2007/0275455 A1 | 11/2007 | Hung et al. |
| 2008/0038713 A1 | 2/2008 | Gao et al. |
| 2008/0085556 A1 | 4/2008 | Graefing et al. |
| 2008/0176318 A1 | 7/2008 | Wilson et al. |
| 2008/0194012 A1 | 8/2008 | Lee et al. |
| 2008/0227176 A1 | 9/2008 | Wilson et al. |
| 2008/0233607 A1 | 9/2008 | Yu et al. |
| 2009/0023608 A1 | 1/2009 | Hung et al. |
| 2009/0123961 A1 | 5/2009 | Meyvantsson et al. |

(56) References Cited

U.S. PATENT DOCUMENTS

| | | | |
|---|---|---|---|
| 2009/0148933 | A1 | 6/2009 | Battrell et al. |
| 2009/0203126 | A1 | 8/2009 | Hung et al. |
| 2010/0151571 | A1 | 6/2010 | Vukasinovic et al. |
| 2010/0196908 | A1 | 8/2010 | Opalsky et al. |
| 2010/0234674 | A1 | 9/2010 | Wheeler et al. |
| 2012/0164036 | A1 | 6/2012 | Stern et al. |
| 2013/0059322 | A1 | 3/2013 | Hung et al. |
| 2013/0081757 | A1 | 4/2013 | Hung et al. |
| 2013/0090268 | A1 | 4/2013 | Hung et al. |
| 2013/0171679 | A1 | 7/2013 | Lee et al. |
| 2013/0171682 | A1 | 7/2013 | Hung et al. |
| 2014/0057311 | A1 | 2/2014 | Kamm et al. |
| 2014/0090735 | A1 | 4/2014 | Hung et al. |
| 2014/0099705 | A1 | 4/2014 | Hung et al. |
| 2014/0287489 | A1 | 9/2014 | Lee et al. |

FOREIGN PATENT DOCUMENTS

| | | |
|---|---|---|
| EP | 0155237 A2 | 9/1985 |
| EP | 0155237 | 9/1995 |
| EP | 0725134 | 8/1996 |
| EP | 0890636 | 1/1999 |
| GB | 1539263 | 1/1979 |
| WO | WO 91/15570 | 10/1991 |
| WO | WO 00/56870 | 9/2000 |
| WO | WO 00/60352 | 10/2000 |
| WO | WO 00/78932 | 10/2000 |
| WO | WO 01/92462 | 12/2001 |
| WO | WO 03/085080 | 10/2003 |
| WO | WO 03/098218 | 11/2003 |
| WO | WO 2004/059299 | 7/2004 |
| WO | WO 2004/106484 | 12/2004 |
| WO | WO 2005/035728 | 4/2005 |
| WO | WO 2007/008606 | 1/2007 |
| WO | WO 2007008609 A2 * | 1/2007 |
| WO | 2009/089189 A2 | 7/2009 |
| WO | 2009/102453 A2 | 8/2009 |

OTHER PUBLICATIONS

Chang et al. (2006) "Fabrication of polymer microlens arrays using capillary forming with a soft mold of microholes array and UV-curable polymer." Optical Society of America 14(13): 6253-6258.

Chao et al. (2007) "Rapid frabrication of microchannels using microscale plasma activated templating (µPLAT) generating water molds." The Rolay Society of Chemistry, 7: 641-643.

Degenaar et al. (2001) "A Method of Micrometer Resolution Patterning of Primary Culture Neurons for SPM Analysys." J. Bio Chem. 367-376.

EP Search Report for application No. 06786499.1 dated Apr. 3, 2012.

US 6,465,252 (withdrawn).

CellASIC Corporation (2012) "ONIX Application Note: microincubator for long term."

Hung et al. (2005) "Continuous perfusion microfludic cell culture array for high -throughput cell-bases assays." Biotechnigues and Bioengineering 89(1): 1-8.

Lee et al. (2007) "Microfluidic System for Automated Cell-Based Assays." Lab Chip 9(1): 164-166.

Lee et al.. (2007) "Microfluidic System for Automated Cell-Based Assays." JALA 12(6): 363-367.

Lim et al. (2003) "Fabrication of Microfludic Mixers and Artifical Vasculatures Using a High-Brightness Diode-Pumped Nd:YAG Lader Direct Write Method." Lap Chip 3: 318-323.

Ong et al. (2008) "A gel-free 3D microfluidic cell culture system." Biomaterials 29(22): 3237-3244.

Runyon et al. (2004) Minimal Functional Model of Hemistasis in a Biomimetic Microfluidit System. Amgew Chem. Intl. Ed. 43: 1531-1536.

Tan et al. (2003) "Microfludic Patterning of Cellular Biopolymer Matrices for Biomimetic 3-D structures." Biomedical Microdivices 5(3): 235-244.

Final Rejection mailed Apr. 11, 2014 in co-pending U.S. Appl. No. 13/436,992.

Office Action mailed Mar. 6, 2014 in co-pending U.S. Appl. No. 13/692,869.

Final Rejection mailed Apr. 4, 2014 in co-pending U.S. Appl. No. 11/994,997.

International Search Report and Written Opinion mailed Apr. 9, 2009 in PCT application No. PCT/US06/26364 (corresponding to U.S. Appl. No. 11/994,997).

International Search Report and Written Opinion mailed Jul. 30, 2009 in PCT application No. PCT/US2009/030168.

Extended European Search report mailed Oct. 21, 2013 in European patent application No. EP 09701350.

International Search Report mailed May 14, 2013 in PCT application No. PCT/US2013/024999.

International Search Report mailed Mar. 19, 2013 in PCT application No. PCT/US2012/067632.

Lab Chip, 2005, vol. 5, No. 4, pp. 401-406, "Human neural stem growth and differentiation in a gradient-generating microfluidic device", Chung, et al.

Lab Chip, 2008, vol. 8, No. 1, pp. 34-57, "Biomolecular gradients in cell culture systems", Keenan, et al.

Biotechnology and Bioengineering, vol. 97, No. 5, Aug. 1, 2007, pp. 1340-1346, "An Artificial Liver Sinusoid With a Microfluidic Endothelial-Like Barrier for Primary Hepatocyte Culture", Lee, et al.

Lab Chip, 2009, vol. 9, No. 1, pp. 164-166, "Dynamic cell culture: a microfluidic function generator for live cell microscopy", Lee, et al.

Office Action mailed Apr. 25, 2013 in co-pending U.S. Appl. No. 13/602,328.

Notice of Allowance mailed Oct. 28, 2013 in co-pending U.S. Appl. No. 13/602,328.

Office Action mailed Feb. 22, 2013 in co-pending U.S. Appl. No. 13/602,331.

Office Action mailed Jun. 17, 2010 in co-pending U.S. Appl. No. 12/019,857.

Final Rejection mailed Feb. 28, 2011 in co-pending U.S. Appl. No. 12/019,857.

Office Action mailed Sep. 15, 2011 in co-pending U.S. Appl. No. 12/019,857.

Final Rejection mailed May 31, 2012 in co-pending U.S. Appl. No. 12/019,857.

Office Action—Restriction—mailed Jul. 13, 2011 in co-pending U.S. Appl. No. 12/348,907.

Office Action mailed Dec. 23, 2011 in co-pending U.S. Appl. No. 12/348,907.

Final Rejection mailed Sep. 17, 2012 in co-pending U.S. Appl. No. 12/348,907.

Office Action—Restriction—mailed Feb. 22, 2013 in co-pending U.S. Appl. No. 13/436,992.

Office Action mailed Sep. 6, 2013 in co-pending U.S. Appl. No. 13/436,992.

Office Action—Restriction—mailed Oct. 16, 2013 in co-pending U.S. Appl. No. 13/692,869.

Office Action—Restriction—mailed Oct. 7, 2013 in co-pending U.S. Appl. No. 13/761,130.

Office Action—Restriction—mailed Mar. 9, 2011 in co-pending U.S. Appl. No. 11/994,997.

Office Action mailed Jul. 18, 2011 in co-pending U.S. Appl. No. 11/994,997.

Final Rejection mailed Feb. 8, 2012 in co-pending U.S. Appl. No. 11/994,997.

Office Action mailed Sep. 11, 2013 in co-pending U.S. Appl. No. 11/994,997.

Lab on a Chip, 2007, vol. 7, pp. 763-769, "A hydrogel-based microfluidic device for the studies of directed cell migration", Cheng, et al.

Lab on a Chip, 2009, vol. 9, p. 1797-1800, "Selective and tunable gradient device for cell culture and chemotaxis study", Kim, et al.

Biomed Microdevices (2008), vol. 10, pp. 499-507, "Microfluidic switching system for analyzing chemotaxis responses of wortmannin-inhibited HL-60 cells", Liu, et al.

(56) References Cited

OTHER PUBLICATIONS

Lab on a Chip, 2007, vol. 7, pp. 1673-1680, "Gradient generation by an osmotic pump and the behavior of human mesenchymal stem cells under the fetal bovine serum concentration gradient", Park, et al.
Notice of Allowance mailed Jan. 13, 2014 in co-pending U.S. Appl. No. 13/602,328.
Notice of Allowance mailed Nov. 13, 2013 in co-pending U.S. Appl. No. 13/602,331.
Notice of Allowance mailed Dec. 23, 2013 in co-pending U.S. Appl. No. 13/602,331.
Office Action mailed Dec. 31, 2013 in co-pending U.S. Appl. No. 13/761,130.
International Preliminary Report on Patentability mailed Jun. 12, 2014 in co-pending PCT application No. PCT/US2012/067632.
Engineering Aspects of Food Biotechnology, Chapter 5, CRC Press: Boca Raton, FL, 2004, copyright 2014, p. 127, "Meet the Stem Cells; Production of Cultured Meat from a Stem Cell Biology Perspective", Brinkhof, et al., 3 pages.
Notice of Allowance mailed Jul. 2, 2014 in co-pending U.S. Appl. No. 13/692,869.
Final Rejection mailed Jun. 25, 2014 in co-pending U.S. Appl. No. 13/761,130.
Notice of Allowance mailed Jul. 31, 2015 in co-pending U.S. Appl. No. 13/692,869.
Notice of Allowance mailed Aug. 4, 2015 in co-pending U.S. Appl. No. 13/761,130.
Notice of Allowance mailed Aug. 24, 2015 in co-pending U.S. Appl. No. 14/081,314.
Final Rejection mailed Mar. 23, 2015 in co-pending U.S. Appl. No. 13/436,992.
Notice of Allowance mailed Apr. 27, 2015 in co-pending U.S. Appl. No. 12/019,857.
Office Action mailed May 13, 2015 in co-pending U.S. Appl. No. 14/053,688.
Notice of Allowance mailed May 6, 2015 in co-pending U.S. Appl. No. 13/761,130.
Notice of Allowance mailed May 4, 2015 in co-pending U.S. Appl. No. 14/081,314.
Office Action mailed Jun. 19, 2015 in co-pending U.S. Appl. No. 14/221,615.
Notice of Allowance mailed Jun. 22, 2015 in co-pending U.S. Appl. No. 11/994,997.
Lab Chip, 2005, vol. 5, pp. 44-48, "A novel high aspect ratio microfluidic design to provide a stable and uniform microenvironment for cell growth in a high throughput mammalian cell culture array", Hung, et al.
Office Action mailed Oct. 7, 2014 in co-pending U.S. Appl. No. 12/019,857.
Notice of Allowance mailed Dec. 22, 2014 in co-pending U.S. Appl. No. 12/348,907.
Office Action mailed Nov. 6, 2014 in co-pending U.S. Appl. No. 13/436,992.
Office Action mailed Oct. 27, 2014 in co-pending U.S. Appl. No. 13/761,130.
Office Action mailed Sep. 15, 2014 in co-pending U.S. Appl. No. 14/081,314.
Advisory Action mailed Jul. 24, 2014 in co-pending U.S. Appl. No. 11/994,997.
Office Action mailed Jan. 26, 2015 in co-pending U.S. Appl. No. 11/994,997.
Notice of Allowance mailed Dec. 10, 2015 in co-pending U.S. Appl. No. 12/019,857.
Office action mailed Nov. 20, 2015 in co-pending U.S. Appl. No. 13/436,992.
Notice of Allowance mailed Jan. 6, 2016 in co-pending U.S. Appl. No. 14/221,615.
Japanese communication, with English translation, dated Nov. 17, 2015 in co-pending Japanese patent application No. 2015-503203.
Keenan et al., "A new method for studying gradient-induced neutrophil desensitization based on an open microfluidic chamber", Lab Chip, 2010, vol. 10, pp. 116-122.
Lee et al., "Microfluidic Systems for Live Cell Imaging", Methods in Cell Biology, 2011, vol. 102, pp. 77-103.
Notice of Allowance mailed Jan. 13, 2016 in co-pending U.S. Appl. No. 14/053,688.
Notice of Allowance mailed Jan. 20, 2016 in co-pending U.S. Appl. No. 12/348,907.
Final rejection mailed Mar. 11, 2016 in co-pending U.S. Appl. No. 13/436,992.
Notice of Allowance mailed Feb. 4, 2016 in co-pending U.S. Appl. No. 13/761,130.
Notice of Allowance mailed Feb. 22, 2016 in co-pending U.S. Appl. No. 14/081,314.
Notice of Allowance mailed Mar. 31, 2016 in co-pending U.S. Appl. No. 12/019,857.
European communication dated Jul. 28, 2015 in co-pending European patent application No. 12852539.1.
Notice of Allowance mailed Sep. 21, 2015 in co-pending U.S. Appl. No. 14/053,688.
Notice of Allowance mailed Oct. 13, 2015 in co-pending U.S. Appl. No. 12/348,907.

* cited by examiner

Cells are cultured in this area

4μm wide and 40μm tall channels prevent cells from growing out.

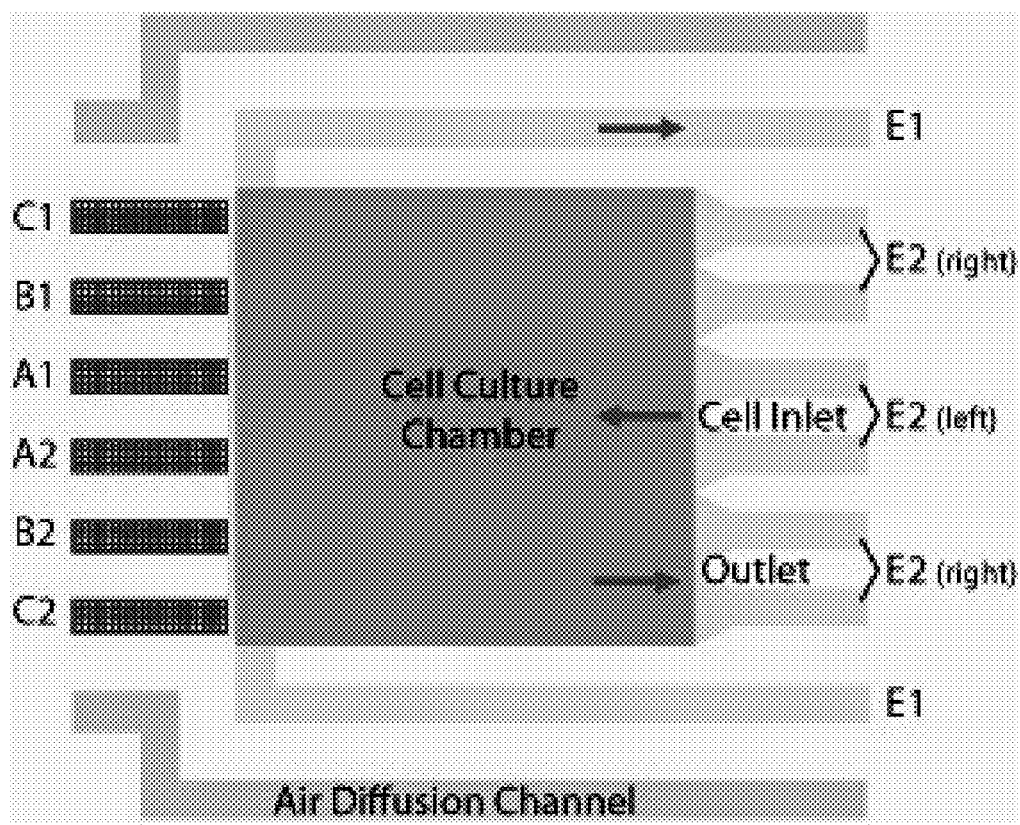
FIG. 6A (SIX WELLS UPSTREAM)

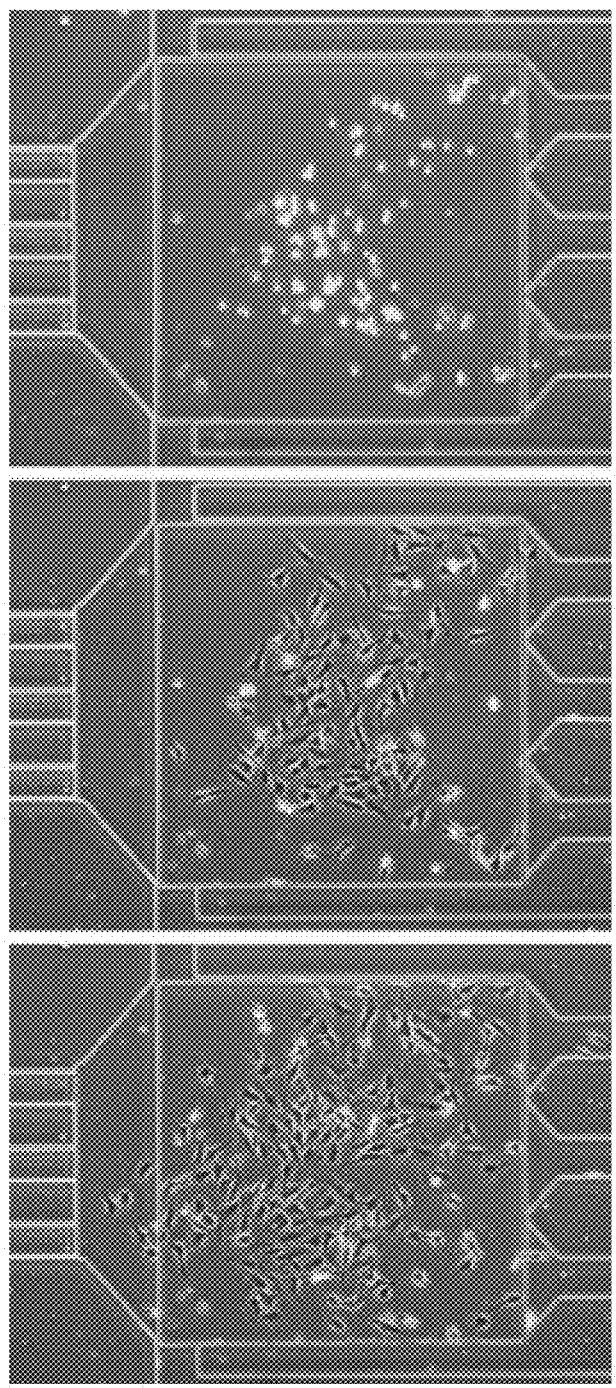
*FIG. 7D (lower cells spread out on surface)*

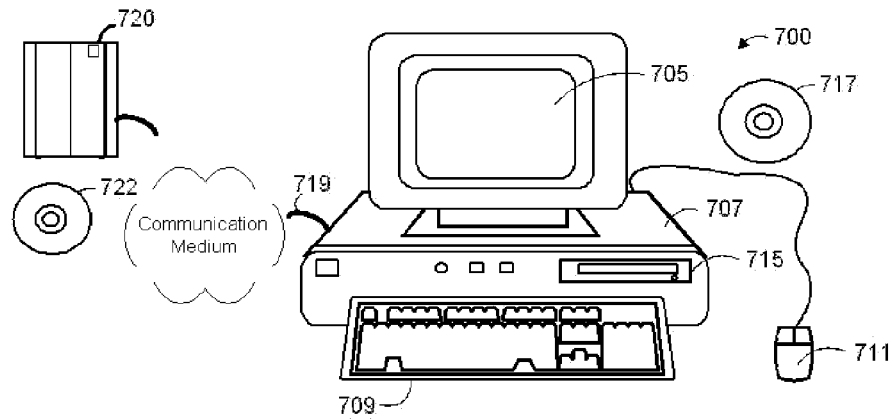

*FIG. 30*

| Disease Classification | Disease |
|---|---|
| Cardiovascular Disease | Atherosclerosis; Unstable angina; Myocardial Infarction; Restenosis after angioplasty or other percutaneous intervention; Congestive Heart Failure; Myocarditis; Endocarditis; Endothelial Dysfunction; Cardiomyopathy |
| Endocrine Disease | Diabetes Mellitus I and II; Thyroiditis; Addisson's Disease |
| Infectious Disease | Hepatitis A, B, C, D, E; Malaria; Tuberculosis; HIV; Pneumocystis Carinii; Giardia; Toxoplasmosis; Lyme Disease; Rocky Mountain Spotted Fever; Cytomegalovirus; Epstein Barr Virus; Herpes Simplex Virus; Clostridium Dificile Colitis; Meningitis (all organisms); Pneumonia (all organisms); Urinary Tract Infection (all organisms); Infectious Diarrhea (all organisms) |
| Angiogenesis | Pathologic angiogenesis; Physiologic angiogenesis; Treatment induced angiogenesis |
| Inflammatory/Rheumatic Disease | Rheumatoid Arthritis; Systemic Lupus Erythematosis; Sjogrens Disease; CREST syndrome; Scleroderma; Ankylosing Spondylitis; Crohn's; Ulcerative Colitis; Primary Sclerosing Cholangitis; Appendicitis; Diverticulitis; Primary Biliary Sclerosis; Wegener's Granulomatosis; Polyarteritis nodosa; Whipple's Disease; Psoriasis; Microscopic Polyanngiitis; Takayasu's Disease; Kawasaki's Disease; Autoimmune hepatitis; Asthma; Churg-Strauss Disease; Beurger's Disease; Raynaud's Disease; Cholecystitis; Sarcoidosis; Asbestosis; Pneumoconioses |
| Transplant Rejection | Heart; Lung; Liver; Pancreas; Bowel; Bone Marrow; Stem Cell; Graft versus host disease; Transplant vasculopathy |
| Leukemia and Lymphoma | |

*FIG. 31. (TABLE 1)*

MICROFLUIDIC CELL CULTURE SYSTEMS

CROSS REFERENCE TO RELATED APPLICATIONS

This application claims priority from provisional patent applications:
61/367,371 filed Jul. 23, 2010
61/297,278 filed Jan. 21, 2010
This application is related to material discussed in one or more of the following applications, each of which are incorporated herein by reference for all purposes: provisional patent application 61/037,297 filed Mar. 17, 2008, provisional patent application 61/018,882 filed Jan. 3, 2008, U.S. application Ser. No. 11/994,997, filed Aug. 11, 2008, which is a National Stage Entry of PCT/US06/26364, filed Jul. 6, 2006 and which claims priority from provisional patent application 60/773,467 filed 14 Feb. 2006 and from provisional patent application 60/697,449 filed 7 Jul. 2005, U.S. application Ser. No. 12/019,857, filed Jan. 25, 2008, which claims priority to U.S. Provisional Patent Application No. 60/900,651 filed on Feb. 8, 2007, U.S. application Ser. No. 11/648,207, filed Dec. 29, 2006, which claims priority to U.S. Provisional Patent Application U.S. provisional patent application No. 60/756,399 filed on Jan. 4, 2006, U.S. application Ser. No. 12/348,907, filed 5 Jan. 2009.

COPYRIGHT NOTICE

Pursuant to 37 C.F.R. 1.71(e), applicants note that a portion of this disclosure contains material that is subject to copyright protection (such as, but not limited to, diagrams, device photographs, or any other aspects of this submission for which copyright protection is or may be available in any jurisdiction.). The copyright owner has no objection to the facsimile reproduction by anyone of the patent document or patent disclosure, as it appears in the Patent and Trademark Office patent file or records, but otherwise reserves all copyright rights whatsoever.

FIELD OF THE INVENTION

The invention in various embodiments relates to handling of micro-objects, such as cells or micro-fabricated particles such as beads, using microfluidic systems. Particular embodiments involve configurations that can be used with various standard automated handling systems and with cells or other objects embedded in a gel. Other particular embodiments involve configurations that can be used with an open cell culture chamber.

BACKGROUND OF THE INVENTION

The discussion of any work, publications, sales, or activity anywhere in this submission, including in any documents submitted with this application, shall not be taken as an admission that any such work constitutes prior art. The discussion of any activity, work, or publication herein is not an admission that such activity, work, or publication existed or was known in any particular jurisdiction.

Microfluidic cell culture is an important technology for applications in drug screening, tissue culturing, toxicity screening, and biologic research and can provide improved biological function, higher-quality cell-based data, reduced reagent consumption, and lower cost. High quality molecular and cellular sample preparations are important for various clinical, research, and other applications. In vitro samples that closely represent their in vivo characteristics can potentially benefit a wide range of molecular and cellular applications. Handling, characterization, culturing, and visualization of cells or other biologically or chemically active materials (such as beads coated with various biological molecules) has become increasingly valued in the fields of drug discovery, disease diagnoses and analysis, and a variety of other therapeutic and experimental work.

Publications and/or patent documents that discuss various strategies related to cell culture using microfluidic systems and related activities include the following U.S. patent applications and non-patent literature, which, along with all citations therein, are incorporated herein by reference for all purposes. A listing of these references here does not indicate the references constitute prior art.

Cytoplex, Inc. U.S. Pat. No. 6,653,124 "Array-based microenvironment for cell culturing, cell monitoring and drug-target validation."

Cellomics, Inc. U.S. Pat. No. 6,548,263 "Miniaturized cell array methods and apparatus for cell-based screening."

Fluidigm, Inc. Published Application 20040229349 (Nov. 18, 2004) "Microfluidic particle-analysis systems."

Other References I
1. T. H. Park and M. L. Shuler, Biotechnol. Prog., 2003, 19, 243.
2. G. M. Walker, H. C. Zeringue and D. J. Beebe, Lab Chip, 2004, 4, 91.
3. E. Leclerc, Y. Sakai and T. Fujii, Biotechnol. Prog., 2004, 20, 750.
4. M. J. Powers, K. Domansky, M. R. Kaazempur-Mofrad, A. Kalezi, A. Capitano, A. Upadhyaya, P. Kurzawski, K. E. Wack, D. B. Stolz, R. Kamm and L. G. Griffith, Biotechnol. Bioeng., 2002, 78, 257.
5. K. Viravaidya and M. L. Shuler, Biotechnol. Prog., 2004, 20, 590.
6. Y. Kostov, P. Harms, L. Randers-Eichhorn and G. Rao, Biotechnol. Bioeng., 2001, 72, 346.
7. N. Li Jeon, H. Baskaran, S. K. Dertinger, G. M. Whitesides, L. Van der Water and M. Toner, Nat. Biotechnol., 2002, 20, 826.
8. T. Thorsen, S. J. Maerkl and S. R. Quake, Science, 2002, 298, 580.
9. H. Andersson and A. van den Berg, *Lab Chip,* 2004, 4, 98.
Other References II
10. Dove, A. (2003) Nature Biotechnology 21, 859-864.
11. Entzeroth, M. (2003) Current Opinion in Pharmacology 3, 522-529.
12. Boess, F.; Kamber, M.; Romer, S.; Gasser, R.; Muller, D.; Albertini, S.; Suter, L. Toxicol Sci 2003, 73, (2), 386-402.
13. Rodriguez-Antona, C.; Donato, M. T.; Boobis, A.; Edwards, R. J.; Watts, P. S.; Castell, J. V.; Gomez-Lechon, M. J. Xenobiotica 2002, 32, (6), 505-20.
14. Cukierman, E.; Pankov, R.; Stevens, D. R.; Yamada, K. M. Science 2001, 294, (5547), 1708-12.
15. Griffith, L. G.; Swartz, M. A. Nat Rev Mol Cell Biol 2006, 7, (3), 211-24.
16. Revzin, A.; Rajagopalan, P.; Tilles, A. W.; Berthiaume, F.; Yarmush, M. L.; Toner, M. Langmuir 2004, 20, (8), 2999-3005.
17. Flaim, C. J.; Chien, S.; Bhatia, S. N. Nat Methods 2005, 2, (2), 119-25.
18. Anderson, D. G.; Levenberg, S.; Langer, R. Nat Biotechnol 2004, 22, (7), 863-6.
19. Battle, T.; Stacey, G. Cell Biol Toxicol 2001, 17, (4-5), 287-99.
20. LeCluyse, E. L.; Bullock, P. L.; Parkinson, A. Advanced Drug Delivery Reviews 1996, (22), 133-186.

21. Ben-Ze'ev, A.; Robinson, G. S.; Bucher, N. L.; Farmer, S. R. Proc Natl Acad Sci USA 1988, 85, (7), 2161-5.
22. Bhatia, S. N.; Balis, U. J.; Yarmush, M. L.; Toner, M. Faseb J 1999, 13, (14), 1883-900.
23. Berthiaume, F.; Moghe, P. V.; Toner, M.; Yarmush, M. L. Faseb J 1996, 10, (13), 1471-84.
24. Stevens, M. M.; George, J. H. Science 2005, 310, (5751), 1135-8.
25. Bissell, M. J.; Rizki, A.; Mian, I. S. Curr Opin Cell Biol 2003, 15, (6), 753-62.
26. Allen, J. W.; Bhatia, S. N. Biotechnol Bioeng 2003, 82, (3), 253-62.
27. Hung, P. J.; Lee, P. J.; Sabounchi, P.; Aghdam, N.; Lin, R.; Lee, L. P. Lab Chip 2005, 5, (1), 44-8.
28. Lee, P. J.; Hung, P. J.; Rao, V. M.; Lee, L. P. Biotechnol Bioeng 2005.
29. Puhl, G.; Schaser, K. D.; Vollmar, B.; Menger, M. D.; Settmacher, U. Transplantation 2003, 75, (6), 756-61.
30. Park, J.; Berthiaume, F.; Toner, M.; Yarmush, M. L.; Tilles, A. W. Biotechnol Bioeng 2005, 90, (5), 632-44.
31. Anderson, K.; Wilkinson, R.; Grant, M. H. Int J Artif Organs 1998, 21, (6), 360-4.
32. Landry, J.; Bernier, D.; Ouellet, C.; Goyette, R.; Marceau, N. J Cell Biol 1985, 101, (3), 914-23.
33. A. Ben-Ze'ev, G. S. Robinson, N. L. Bucher, S. R. Farmer, Proc Natl Acad Sci USA 85, 2161 (April, 1988).
34. J. Landry, D. Bernier, C. Ouellet, R. Goyette, N. Marceau, J Cell Biol 101, 914 (September, 1985).
35. S. A. Stoehr, H. C. Isom, Hepatology 38, 1125 (November, 2003).
36. Zhang, X, Wang, W, Yu, W, Xie, Y, Zhang, X, Zhang, Y, Ma, X. Biotechnol Prog 2005, 21, 1289-96.
37. Kelm, J, Timmins, N, Brown, C, Fussenegger, M, Nielsen, L. Biotechnology and Bioengineering. 2003, 83(2)173-180.
38. Kuns-Schughart, L, Freyer, J, Hofstaedter, F, Ebner, R. J. Biomolecular Screening. 2004, 9(4) 273-285.

Earlier work and patent applications as cited above, involving at least one of the present inventors, discuss various configurations, methods, and systems related to microfluidic cell culture and that work and those publications are is incorporated herein by reference.

SUMMARY

The present invention involves various components, systems, and methods related to improved microfluidic cell culture devices and systems. In one aspect, the invention involves novel microfluidic cell culture devices, systems and methods that have advantages over previously proposed microfluidic structures. In another aspect, the invention involves novel structures and methods for integrating multiple microfluidic cell culture units into various multi cell culture unit systems, such as to a microtiter well plate structure, such as a standard well plate formats (e.g., a 96-well SBS culture plate, or other plate formats, including plates having 6, 12, 24, 96, 384 or 1536 sample wells, as well as open bottom standard well plates, allowing for attachment to microfluidic structures as described herein.). In a further aspect, the invention involves novel fabrication methods for creating an array of microfluidic cell culture units or areas suitable for integration with a well plate. In another aspect, the invention involves novel systems, methods, and components for an improved automated high-throughput cell culture and/or screening system using microfluidic cell culture devices and systems. In other aspects, the invention involves novel culture chamber designs and systems for providing effective culture of cells in various situations, including cells cultured in a gel 3D matrix. In other aspects, the invention involves novel cell culture chamber designs and systems allowing use of open-top cell culture chambers with the invention providing sufficiently controlled flow of culture media to prevent the media from flowing out of the open top culture area. In other aspects, the invention involves use of customized or partly customized well-plates along with one or more standard or customized well plate loading or handling systems to provide culture units that in part interface with standard plate designs and in part skip cells or combine cells into culture units.

In particular embodiments and examples, design features include the elimination of tubing and connectors to the plates themselves, the ability to maintain long-term continuous perfusion cell culture using a passive gravity-driven flow, the ability to perform direct analysis on the outlet wells and/or cellular observation wells or culture wells of the microfluidic plate, the ability to effectively handle gel culture media, and the ability to effectively allow open culture wells in microfluidic systems.

While many of the examples discussed in detail herein are designed to be used in conjunction with a standard or custom well plate, the microfluidic structures and culture units and systems and methods of various configurations as described herein can also be deployed independently of any well-plate, such as in various integrated lab-on-a-chip systems that are not configured to be used in conjunction with well plates or various other microfluidic devices or systems.

For purposes of clarity, this discussion refers to devices, methods, and concepts in terms of specific examples. However, the invention and aspects thereof may have applications to a variety of types of devices and systems. It is therefore intended that the invention not be limited except as provided in the attached claims and equivalents.

Furthermore, it is well known in the art that systems and methods such as described herein can include a variety of different components and different functions in a modular fashion. Different embodiments of the invention can include different mixtures of elements and functions and may group various functions as parts of various elements. For purposes of clarity, the invention is described in terms of systems that include many different innovative components and innovative combinations of innovative components and known components. No inference should be taken to limit the invention to combinations containing all of the innovative components listed in any illustrative embodiment in this specification. Unless specifically stated otherwise herein, any combination of elements described herein should be understood to include every sub-combination of any subset of those elements and also any sub-combination of any subset of those elements combined with any other element described herein as would be understood to a practitioner of skill in the art.

In some of the drawings and detailed descriptions below, the present invention is described in terms of the important independent embodiments of multi-component devices or systems. This should not be taken to limit various novel aspects of the invention, which, using the teachings provided herein, can be applied to a number of other situations. In some of the drawings and descriptions below, the present invention is described in terms of a number of specific example embodiments including specific parameters related to dimensions of structures, pressures or volumes of liquids, temperatures, electrical values, durations of time, and the like. Except where so provided in the attached claims, these parameters are provided as examples and do not limit the invention, which encompasses other devices or systems with different dimensions. For purposes of providing a more illuminating description, particular known fabrication steps, cell handling steps, reagents, chemical or mechanical process, and other known components that may be included to make a system or manufacture a device according to specific embodiments of the invention are given as examples. It will be understood to those of skill in the art that except were specifically noted herein otherwise, various known substitutions can be made in the processes described herein.

All references, publications, patents, and patent applications cited in this submission are hereby incorporated by reference in their entirety for all purposes.

BRIEF DESCRIPTION OF THE DRAWINGS

FIG. 6A-C illustrate configuration and operation of an example roughly rectangular cell culture chamber design according to specific embodiments of the invention.

FIG. 7A-E illustrate configuration and operation of a second example roughly rectangular new cell culture chamber design according to specific embodiments of the invention.

FIG. 30 is a block diagram showing a representative example logic device in which various aspects of the present invention may be embodied.

FIG. 31 (Table 1) illustrates an example of diseases, conditions, or states that can evaluated or for which drugs or other therapies can be tested according to specific embodiments of the present invention.

DETAILED DESCRIPTION OF SPECIFIC EMBODIMENTS

1. Overview

Definitions

Figure 1:
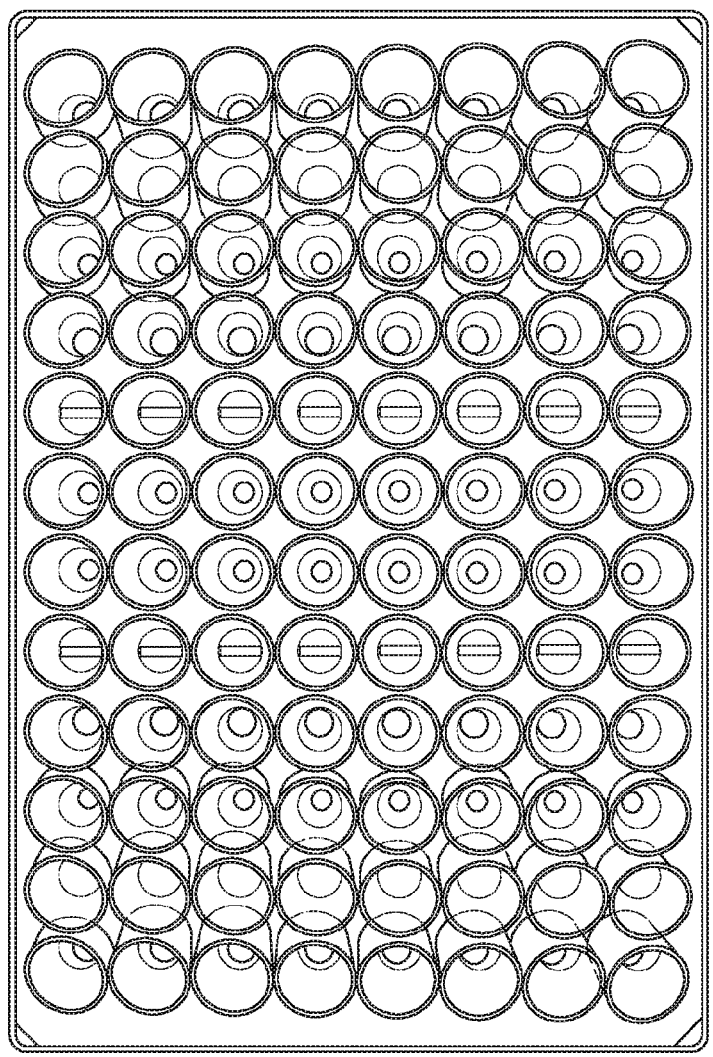
FIG. 1 is a top view of an example array of cell culture units provided on a 96-well standard SBS plate according to specific embodiments of the invention.

A "particle" refers to biological cells, such as mammalian or bacterial cells, viral particles, or liposomal or other particles that may be subject to assay in accordance with the invention. Such particles have minimum dimensions between about 50-100 nm, and may be as large as 20 microns or more. When used to describe a cell assay in accordance with the invention, the terms "particles" and "cells" may be used interchangeably.

A "microchannel" or "channel" or "flow channel" generally refers to a micron-scale channel used for fluidically connecting various components of systems and devices according to specific embodiments of the invention. A microchannel typically has a rectangular, e.g., square, or rounded cross-section, with side and depth dimensions in a preferred embodiment of between 10 and 500 microns, and 10 and 500 microns, respectively. Fluids flowing in the microchannels may exhibit microfluidic behavior. When used to refer to a microchannel within the microwell array device of the invention, the term "microchannel" and "channel" are used interchangeably. "Flow channel" generally denotes channels designed for passage of media, reagents, or other fluids or gels and in some embodiments cells. "Culture channel" or "cell culture channel" generally denotes a portion of a cell culture structure that cells are designed to flow through and also remain during cell culture (though the cells may be localized into a particular culture area of the culture channel in some embodiments). "Air channel" generally denotes a roughly micron-scale channel used for allowing gases, such as air, oxygen enriched mixtures, etc., to pass in proximity to flow channels or culture areas. "Perfusion channel" is sometimes used to indicate a flow channel and any perfusion passages or structures that allow media to perfuse to the culture area.

A "perfusion barrier" refers to a combination of solid structures and perfusion passages that generally separate a flow channel from a cell culture area or chamber. The perfusion passages are generally smaller than the microchannel height and/or width (for example, on the order of 5-50% or on the order of about 10%) and are designed to keep cells, other culture items, and in some embodiments gels, from migrating into the flow channels, while allowing some fluidic flow that is generally of a much higher fluidic resistance than the fluid flow in the flow channels. In one example embodiment, the perfusion barrier has a perfusion passage that is 4 microns high and that otherwise runs most of the length of the microchannel. In other embodiments, a perfusion barrier has many perfusion passages that are about as high as the microfluidic channel, but about 4 microns wide. In some configurations, a perfusion barrier may also be referred to as an "epithelial barrier."

A "microfluidics device" refers to a device having various station or wells connected by micron-scale microchannels in which fluids will exhibit microfluidic behavior in their flow through the channels.

A "microwell array" refers to an array of two or more microwells formed on a substrate.

A "device" is a term widely used in the art and encompasses a broad range of meaning. For example, at its most basic and least elaborated level, "device" may signify simply a substrate with features such as channels, chambers and ports. At increasing levels of elaboration, the "device" may further comprise a substrate enclosing said features, or other layers having microfluidic features that operate in concert or independently. At its most elaborated level, the "device" may comprise a fully functional substrate mated with an object that facilitates interaction between the external world and the microfluidic features of the substrate. Such an object may variously be termed a holder, enclosure, housing, or similar term, as discussed below. As used herein, the term "device" refers to any of these embodiments or levels of elaboration that the context may indicate.

Microfluidic systems provide a powerful tool to conduct biological experiments. Recently, elastomer-based microfluidics has especially gained popularity because of its optical transparency, gas permeability and simple fabrication methods. However, the interface with the end-users requires labor-intensive hole punching through the elastomer, and additional steps of tubing and syringe pump connection.

The present invention involves integrated microfluidics used for various culture and assay applications. The invention further involves methods of manufacture of microfluidics and components and a system for automating cell culture using such plates. Advantages of specific embodiments include use of a standard microtiter plate format, tubing free cell culture, and a biomimetic liver microenvironment.

A system according to specific embodiments of the invention (for example, using 96-well standard plates) can be operated using standard techniques and equipment for handling standard microtiter plates, as are well known in the art. For example, liquid dispensing is achieved with standard pipette mechanics, and cell culture and analysis can be made compatible with existing incubators and plate readers.

According to further embodiments of the invention, a novel cell loading system uses a pneumatic manifold and pneumatic pressure to place cells in the micro culture area. With the addition of this cell loading system, microfluidic cell culture and analysis can be fully automated using other automated equipment that exists for handling standard titer plates.

In further embodiments, the gravity driven flow culture configuration utilizes the medium level difference between the inlet and outlet well as well as engineering the fluidic resistances to achieve the desirable flow rate in nL/min regime. This provides the significant advantage of being able to "passively" flow culture medium for long periods of time (up to 4 days) without the use of bulky external pumps or tubes.

In further embodiments, the invention involves a microfluidic system to allow control of the cell culture environment for long-term time-lapse microscopy of adherent cells. As the trend towards "systems biology" continues, it will become increasingly important to study dynamic behavior in individual live cells as well as to improve the functionality and economics of high throughput live cell screening. According to specific embodiments of the invention, the invention provides a multiplexed microfluidic flow chamber allowing for time-lapse microscopy experimentation among other assays. The microfluidic chamber uses an artificial endothelial barrier to separate cells from flow channels. The device is formatted to a standard well plate, allowing liquid and cell samples to be directly pipetted into the appropriate inlet reservoirs using standard equipment. A custom pneumatic flow controller is then used to load the cells into the culture regions as well as to switch between different exposure solutions. A digital software interface can be used to allow a user to program specific inputs (pulses, ramps, etc.) over time to expose the cells to complex functions during time-lapse imaging.

Dynamic responses in living cells are the foundation for phenomena such as biological signal processing, gene expression regulation, differentiation, and cell division. In specific embodiments, the invention involves a system capable of controlling the cellular micro-environment in a multiplexed format compatible with current cell culture methods. Cell response can be quantified using high magnification fluorescence microscopy to derive kinetic information with sub-cellular resolution. This capability has broad applications in cellular systems biology where dynamic single cell response experiments are not currently practical.

2. Microfluidic Culture System and Array

The applications referenced above discussed a variety of different cell culture configurations and fabrication techniques. Portions of the operation of the cell culture areas and materials are useful as background to the present discussion. In some examples therein, one or more micro culture areas are connected to a medium or reagent channel via a grid of fluidic passages (or diffusion inlets or conduits), wherein the grid comprises a plurality of intersecting high fluidic resistance perfusion passages. In one discussed example, passages in the grid are about 1 to 4 µm in height, 25 to 50 µm in length and 5 to 10 µm in width, the grid allowing for more even diffusion between medium or reagent channels and the culture area and allowing for easier manufacturing and more even diffusion. The earlier application further discussed that the high fluidic resistance ratio between the microchamber and the perfusion/ diffusion passages or grid (e.g., ratios in the range of about 10:1, 20:1 to 30:1) offers many advantages for cell culture such as: (1) size exclusion of cells; (2) localization of cells inside a microchamber; (3) promoting a uniform fluidic environment for cell growth; (4) ability to configure arrays of microchambers or culture areas; (4) ease of fabrication, and (5) manipulation of reagents without an extensive valve network. Examples were illustrated wherein a grid-like perfusion barrier can be much shorter than the culture area or can be near to or at the same height, according to specific embodiments of the invention and further wherein various configurations for culture devices were illustrated. The application also discussed a CAD drawing of a proposed 96-unit microfluidic bioreactor wherein each well was an SBS standard size (3.5 mm in diameter) in order to be compatible with existing robotic liquid handling systems and plate readers. The application also discussed several different configurations for an artificial sinusoid using both cut passages and grids and with a flow-around perfusion design.

Figure 2:
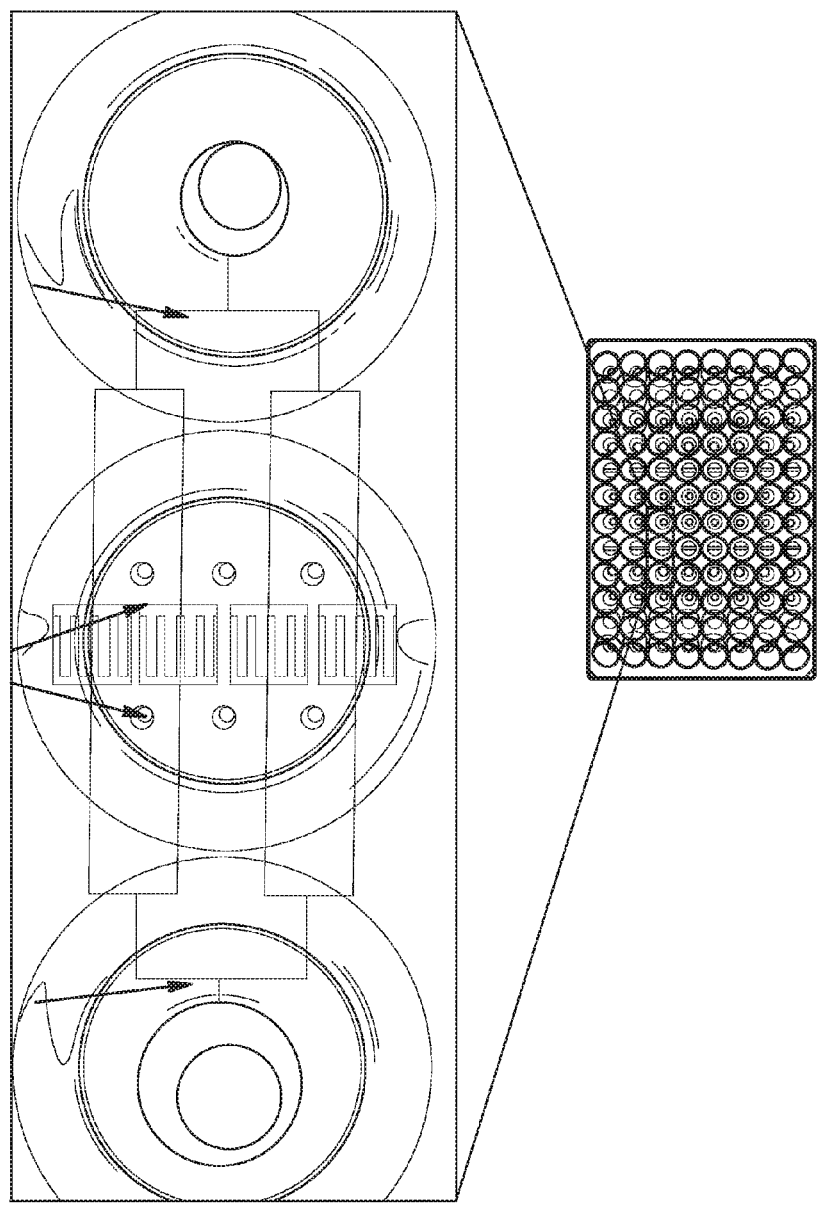
FIG. 2 is an underside view showing one culture unit occupying three wells in an example array according to specific embodiments of the invention.
Figure 3:
FIG. 3 illustrates high aspect ratio channels (also referred to herein as perfusion passages or perfusion barriers) surrounding cell culture areas in an example array according to specific embodiments wherein channels between solid structures are approximately 4 μm wide and 40 μm tall to prevent cells from growing out. The channels in this example are separated by approximately 40 μm solid structures.
Figure 3:

FIG. 1 is a top view of an example array of cell culture units provided on a 96-well standard SBS plate according to specific embodiments of the invention. In this example, 32 culture units are provided on a 96-well plate (such as the Society for Biomolecular Screening (SBS) standard microfluidic bioreactor array schematic), with wells arranged in 12 columns (shown vertically and labeled as is standard in the art, 1-12 from top to bottom) by 8 rows (shown horizontally and labeled as is standard in the art, A-H from left to right). In this example, each cell culture unit occupies three wells, one for use as a medium inlet, one for use as a cell inlet/medium outlet, and one for use for cell imaging (which appears as a dark rectangle in the wells in the figure) and/or for providing air passages to a cell culture area. In specific embodiments, each unit can be used as an independent biomimetic cell. This example is shown for discussion purposes, and any number of other configurations are possible including configurations are described and illustrated in this application or as would be understood or suggested to one of skill in the art having benefit of the teachings provided herein. FIG. 2 through FIG. 3 show further details of structures according to specific embodiments of the invention. For purposes of clarity, each of these figures can be understood as further detail of the example configuration discussed above.

FIG. 2 is an underside view showing one culture unit occupying three wells in an example array according to specific embodiments of the invention. In this example, the cell culture portion visible in the middle well is divided into four blocks, with each block having four separated cell culture areas (or channels) surrounded by medium channels used for medium fluidic passage. In particular embodiments, these four separated cell culture areas may be referred to as sinusoids or artificial sinusoids, regardless of whether the far end of the areas has a rounded shape. Separation into four blocks facilitates air diffusion through the material that defines the microfluidic channels (such as silicone elastomer polydimethylsiloxane (PDMS)) structure into the culture areas. Six air holes to facilitate air passage are shown.

FIG. 3 illustrates high aspect ratio channels (also referred to herein as perfusion passages or perfusion barriers) surrounding cell culture areas in an example array according to specific embodiments wherein channels between solid structures are approximately 4 µm wide and 40 µm tall to prevent cells from growing out. The channels in this example are separated by approximately 40 µm solid structures.

Figure 4A:
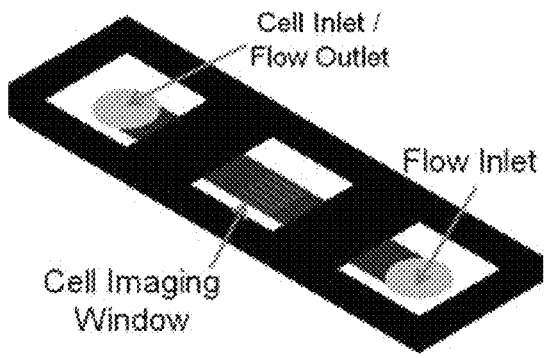
FIG. 4A-B are simplified schematic diagrams illustrating in three dimensions the components of a multi well (e.g., 3) microfluidic system including a representation of the well frame according to specific embodiments of the invention.
Figure 4B:
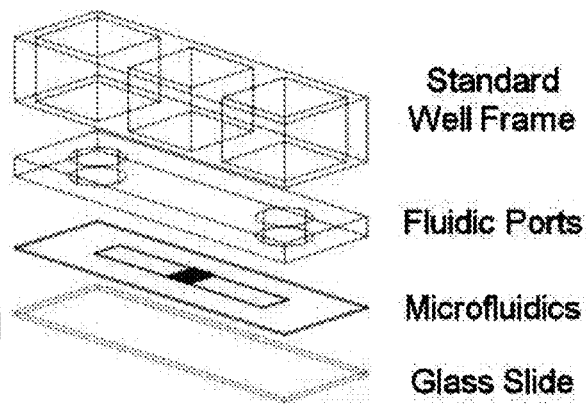

FIG. 4A-B are simplified schematic diagrams illustrating in three dimensions the components of a multi well (e.g., 3) microfluidic system including a representation of the well frame according to specific embodiments of the invention.

Figure 5:
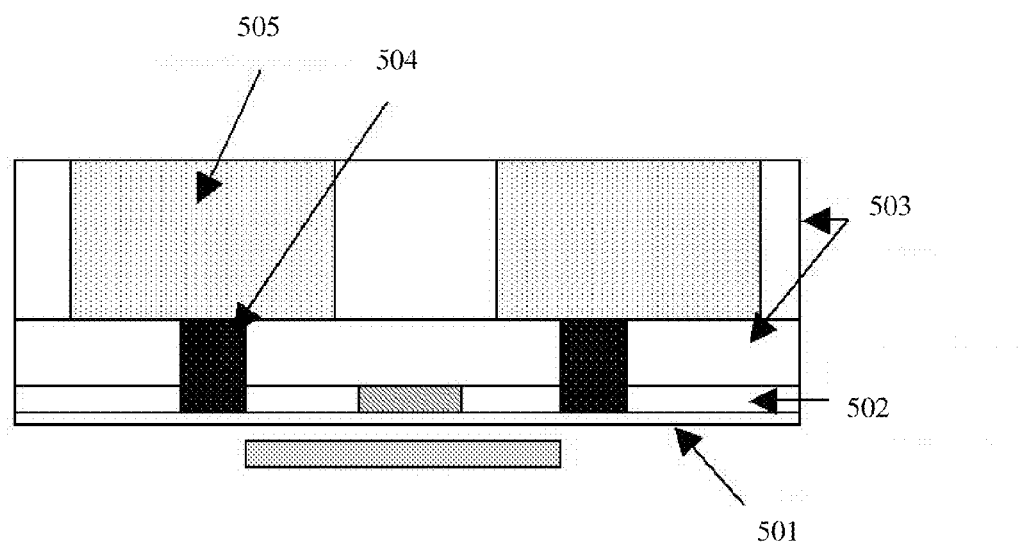
FIG. 5 is a simplified side view showing a structure according to specific embodiments of the invention illustrating two wells that are used in cell flow and fluid flow.
Figure 5:
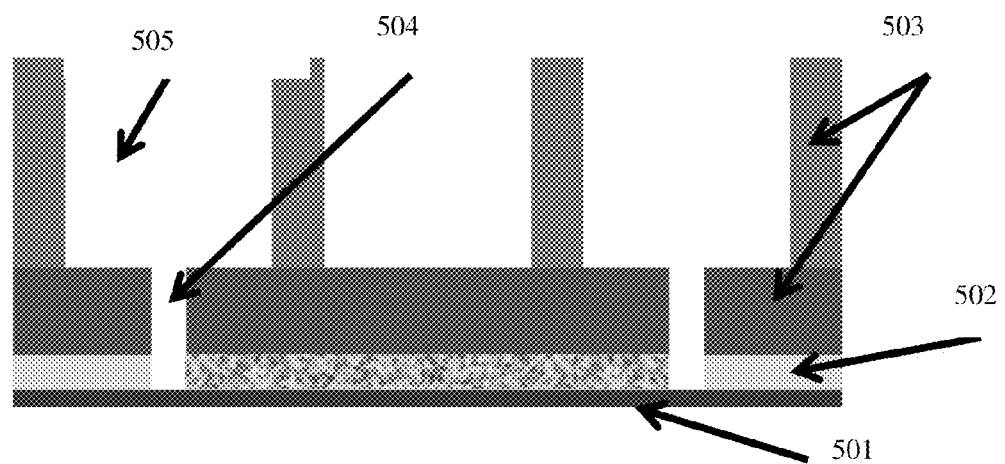

FIG. 5 is a simplified side view showing a structure according to specific embodiments of the invention illustrating two wells that are used in cell flow and fluid flow. Both views show side views of the device and illustrate glass layer 501, microfluidics layer 502, well layer 503, lower reservoir 504, and upper reservoir 505.

Thus, the present invention according to specific embodiments, can be used in a variety of cell culture systems, including novel improved microfluidic systems, methods, designs, devices, and/or configurations as discussed in above referenced applications and incorporated herein by reference. In a first aspect, three wells are used for each otherwise independent cell culture system. In a second aspect, artificial sinusoids with artificial epithelial barriers are provided with just one (optionally shared or multiplexed) fluidic inlet and one (optionally shared or multiplexed) fluidic output, where the medium output also functions as a cellular input. In a third aspect, artificial sinusoids with artificial epithelial barriers with just one fluidic inlet and one fluidic output are divided into blocks with air channels provided between blocks. In a fourth aspect, air holes are provided in the well chamber above the cell culture area of a microfluidic cellular culture array, where the medium output also functions as a cellular input. In a fifth aspect, a multiplexed medium inlet structure and multiplexed cellular input structure are provided to connect inputs and outputs to blocks of artificial sinusoids. In a sixth aspect, a multiplexed medium inlet structure and larger shared cellular input structure are provided to connect inputs and outputs to blocks of artificial sinusoids. In a seventh aspect, artificial sinusoids are configured with non-open portions of an epithelial barrier to better localize cells, and with perfusions inlets surrounding a cell culture area and optionally also present near a cell inlet area of the sinusoid. In an eighth aspect, longer artificial sinusoid chambers are provided.

As discussed elsewhere, various modifications may be made to the cell culture area as described above. Various configurations are possible for the epithelial barrier (or perfusion barrier), such as a grid-like passage structure. Other variations will be suggested to those of skill in the art having the teachings provided herein.

The structures disclosed above can also be adapted to systems using more or fewer wells on a standard microtiter well plate or a fully customized or partially customized plate, such as those described in referenced documents and in other examples herein.

3. Modified Cell Culture Chamber

Plates and systems as described herein can be used with other configurations of cell culture areas or cell culture chambers and micro-fluidic flow structures, including one or more of the novel designs described below.

Figure 6B:
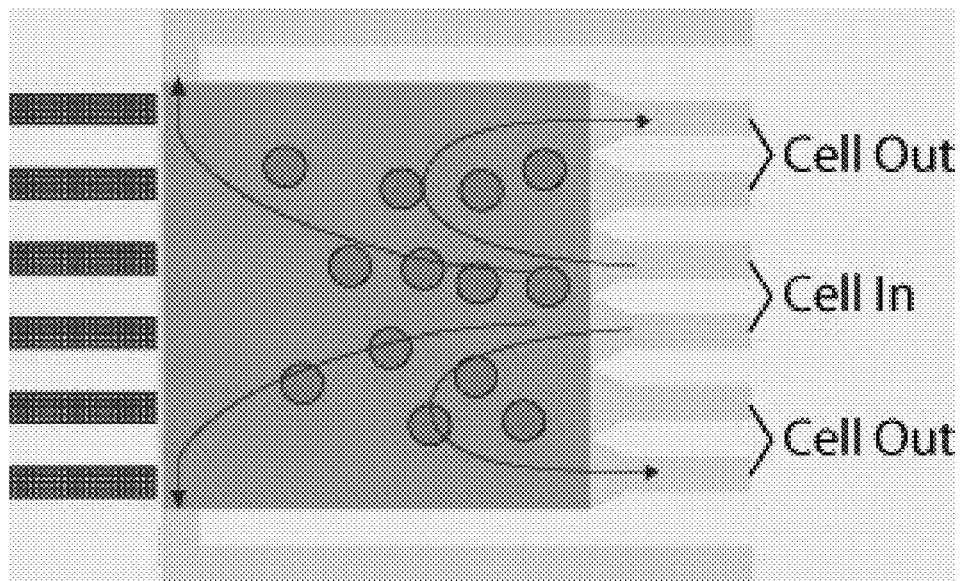
Figure 6C:
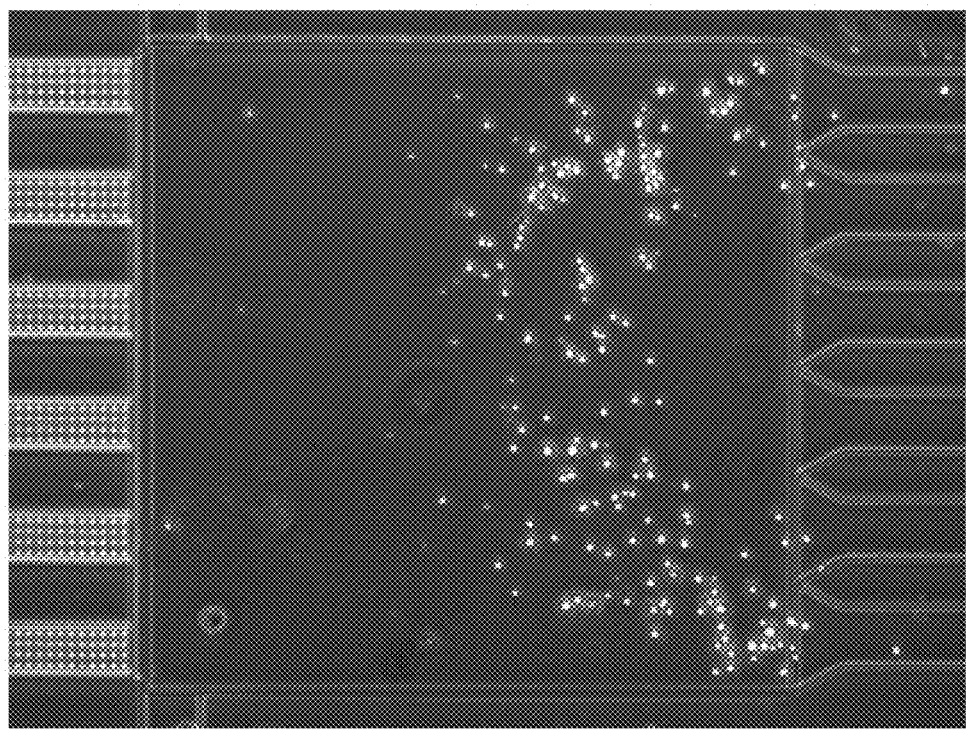

FIG. 6A-C illustrate configuration and operation of an example roughly rectangular cell culture chamber design according to specific embodiments of the invention. In this example design, the cell culture area provided is an essentially rectangular cell culture chamber. The cell culture chamber has cell inlet and outlet passages E2 shown at the right, and flow outlets E1 also shown at the right. In this example, the cell passages are paired, with the center pair used for cell flow loading and the pairs on either side used as a cell flow outlet. Multiple separate flow inlets are shown on the left, labeled A1, A2, B1, B2, C1, C2 and in this example design the flow inlets have a grid pattern to prevent blockage by cells. Air diffusion channels are shown surrounding the chamber. Outlet E1 provides an outlet for fluid flow that is partially isolated from the culture chamber.

FIG. 6B illustrates cell loading in a culture unit as shown in FIG. 6A. Cells are loaded via a low resistance fluidic path (with higher resistance in the flow paths). The cells are prevented from blocking the flow paths by the resistance ratio (the cells preferentially flow to the cell outlet instead of the flow channels). The channels in this particular embodiment are arranged such that the cell in and cell out channels are on the right side of the chamber. This results in the unique feature where flow of cells goes into the chamber, makes a 180 degree turn, and flows out, as illustrated by the sharply curved streamlines shown in FIG. 6B from the Cell In to Cell Out passages.). Thus, according to specific embodiments of the invention, cells are loaded (via capillary force) from the center right channel(s) and out from the top and bottom right channels. A very small amount of flow is directed towards the side outlet channels (the longer less curved streamlines shown in FIG. 6B exiting at the left edge of the chamber). The side flow is not important for cell loading, but serves to help distribute cells more evenly in the chamber. Because of the low velocity of the flow, the cells naturally settle onto the chamber floor without needing any physical barrier. The cell outlet paths help make the loading symmetric, as well as to increase the number of cells loaded into the chamber. This loading mechanism can be used to load cells, particles, beads, gels, gels with cells, etc.

FIG. 6C is a photomicrograph showing cells loaded into a microfluidic chamber as described above.

FIG. 7A-E illustrate configuration and operation of a second example roughly rectangular new cell culture chamber design according to specific embodiments of the invention. This example design differs only slightly from that of FIG. 6 and all operation modes described for one of these two designs herein apply to the other.

Figure 7A:
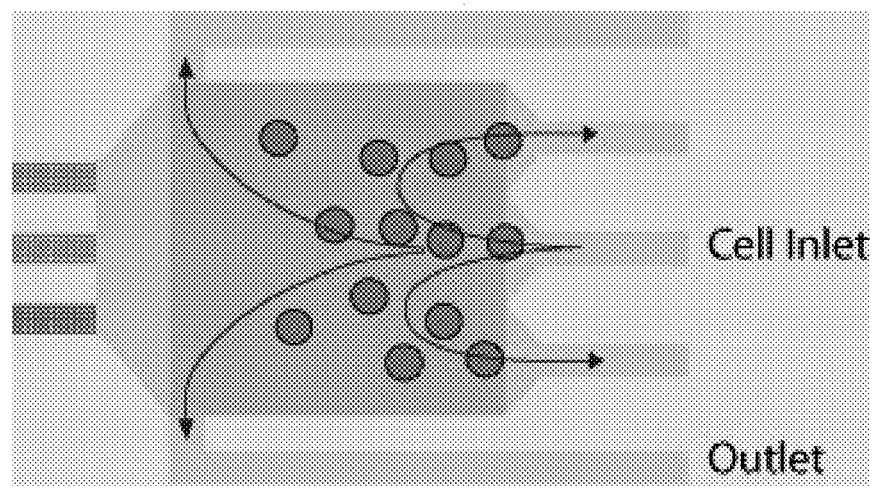

FIG. 7A illustrates cell loading in a culture unit with an essentially rectangular cell culture chamber using with cell inlet and outlet passages shown at the right and flow outlets also shown at the right. In this example, the cell passages are unpaired. Three unpaired flow inlets are shown on the left and these also have a grid pattern to prevent blockage by cells. Air diffusion channels generally are placed near the chamber, though not shown in this figure.

Figure 7B:
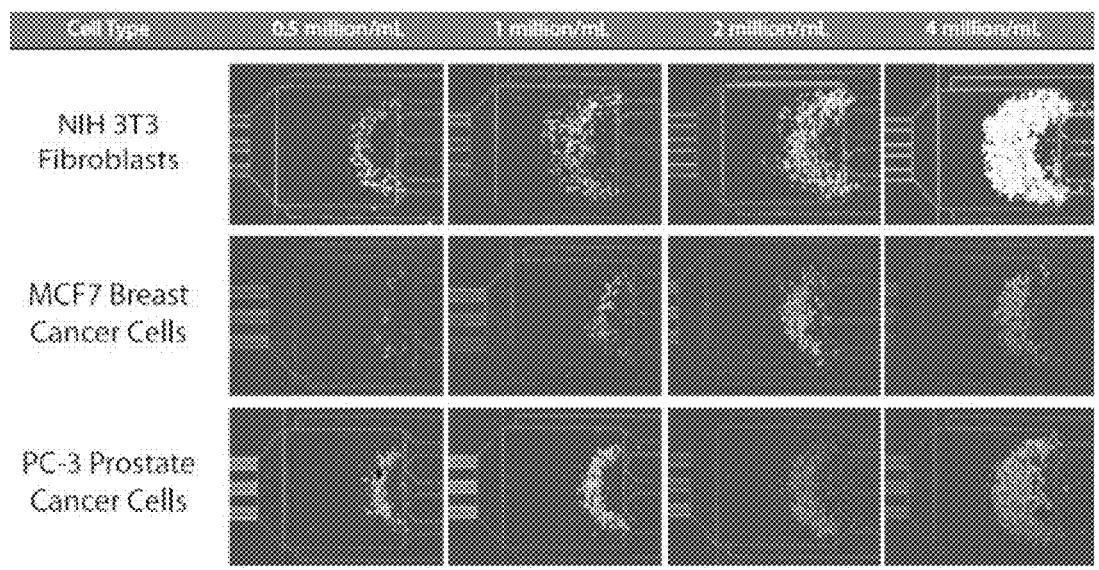

FIG. 7B is a photomicrograph showing three different cell types loaded at four different concentrations of cells loaded into a microfluidic chamber as described above.

Figure 7C:
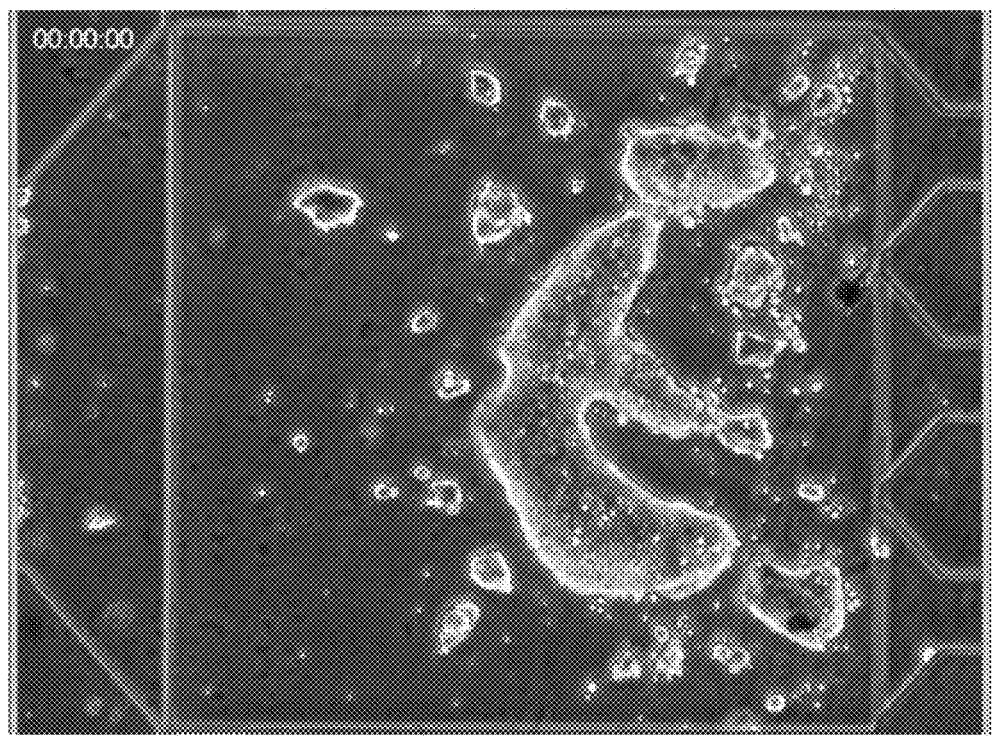

FIG. 7C is a photomicrograph showing a close-up view of mouse embryonic stem cells cultured in the microfluidic device as described above.

FIG. 7D is a photomicrograph showing cell growth in the microfluidic device as described above.

Figure 7E:
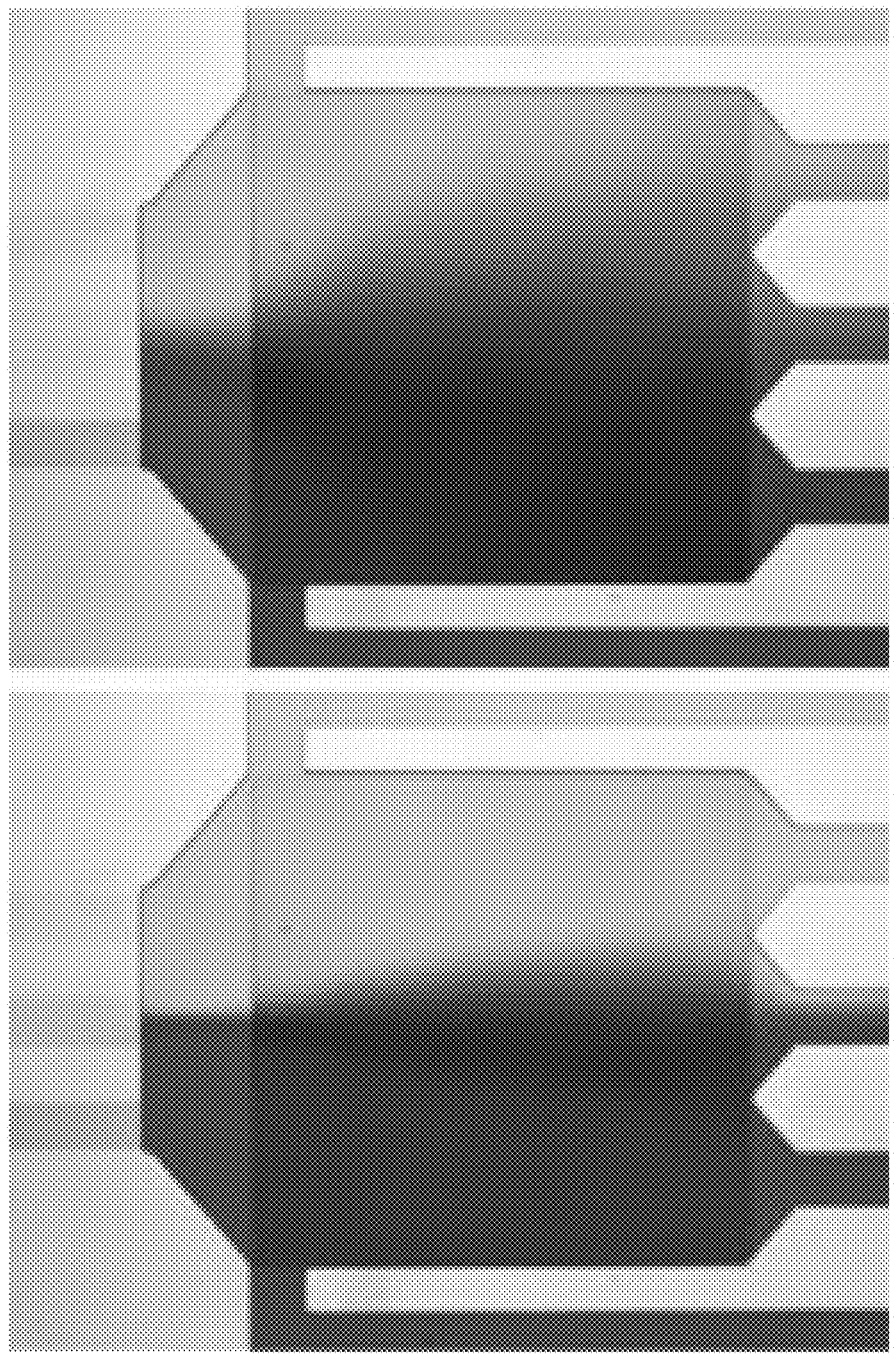

FIG. 7E illustrates creating a gradient in the culture chamber by flowing 2 (or more) solutions at once according to specific embodiments of the invention in the microfluidic device as described above.

4. 3D Cell/Gel Culture Chamber

Figure 8A:
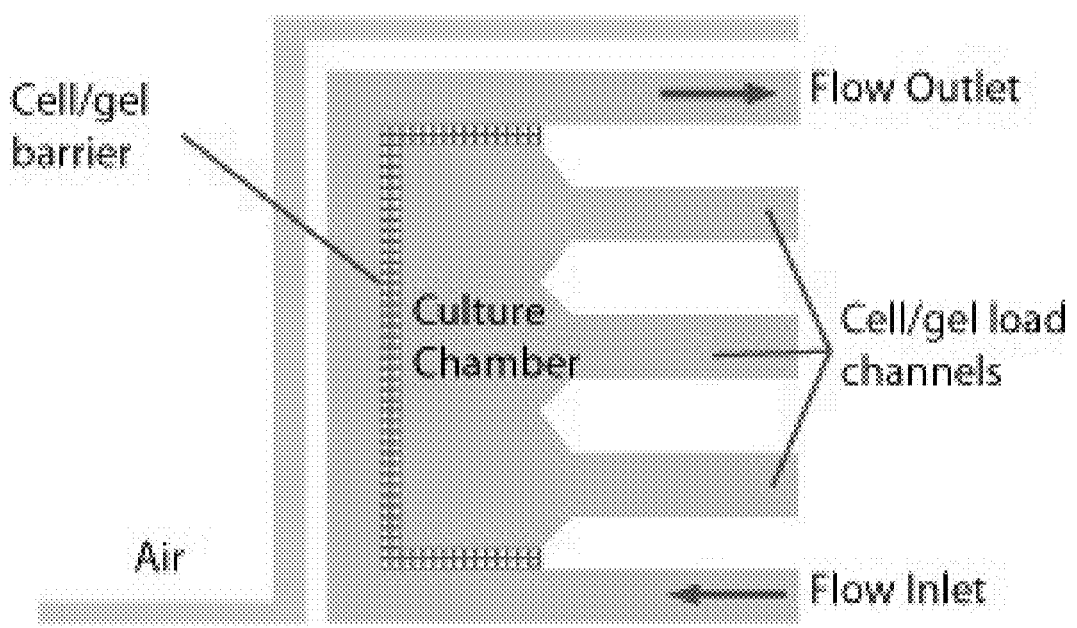
FIG. 8A-8E illustrate configuration and operation of an example cell culture chamber design for 3D gel cell culture according to specific embodiments of the invention.
Figure 8B:
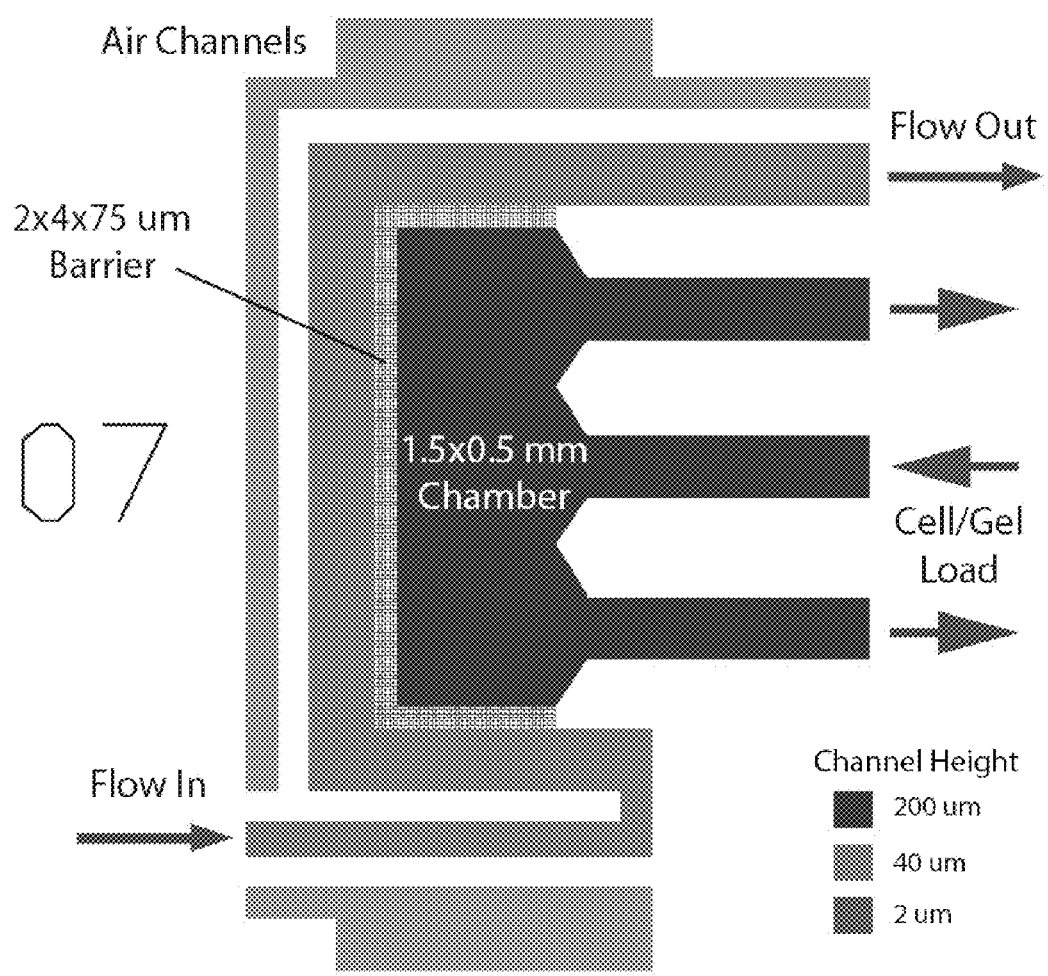
Figure 8C:
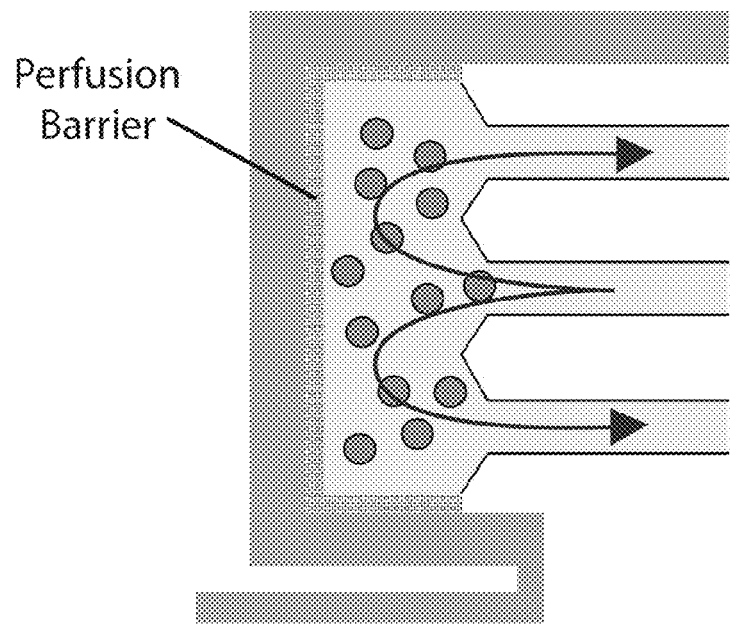

FIG. 8A-C illustrate configuration and operation of an example cell culture chamber design for 3D gel cell culture according to specific embodiments of the invention. This example includes a cell/gel perfusion barrier with a cross-hatch perfusion passage design. The cross hatch design allows cells in a gel matrix to be flowed into the chamber and allows for perfusion of media. While the cross-hatch perfusion barrier is presently preferred in some designs, culture chambers with different perfusion barriers or no perfusion barriers are also implemented according to specific embodiments. A flow around channel for media includes an outlet and inlet both on the same side of the barrier. FIG. 8A illustrates a general embodiment where the outlet and inlet openings are shown to the right. FIG. 8B illustrates an inlet channel to the left and outlet channel to the right, which configuration is better suited in some example systems using a well plate as described herein. This figure also provides detailed example dimensions of a sample design according to specific embodiments of the invention. Thus, in a further embodiment, a cell culture chamber is modified to allow easier culture of cells in 3D gel matrix. In this design, a perfusion barrier separates the cell culture area and the flow channel as illustrated. The barrier is designed to retain a 3D gel in the culture chamber. Coupling the barrier with the 3-channel cell/gel inlet design described above is an important feature that provides improved performance. By having separate flow inlets/outlets on each side of the barrier, it is possible to localize a fluid gel in the culture chamber, and not have it obstruct the flow channel.

Figure 8D:
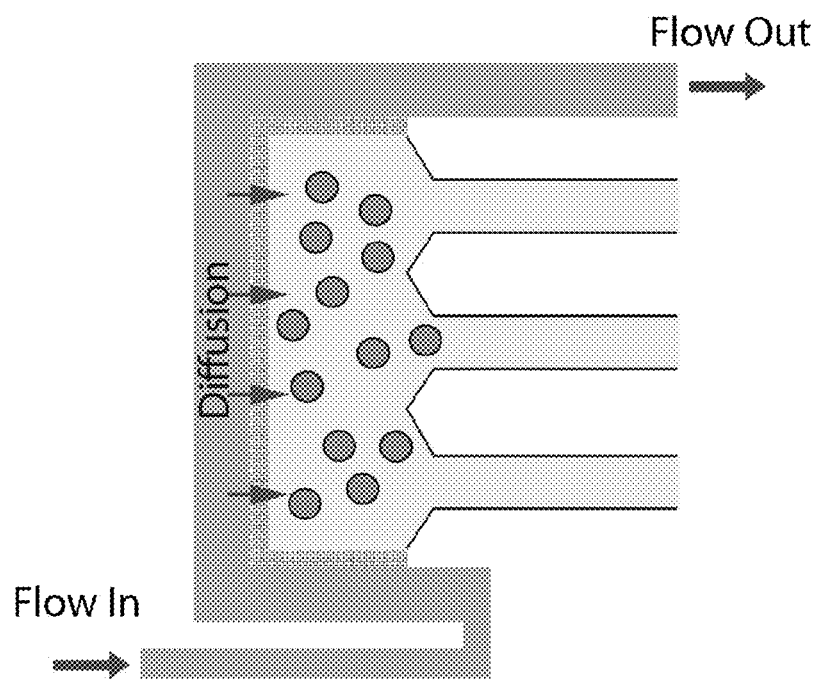
Figure 8E:
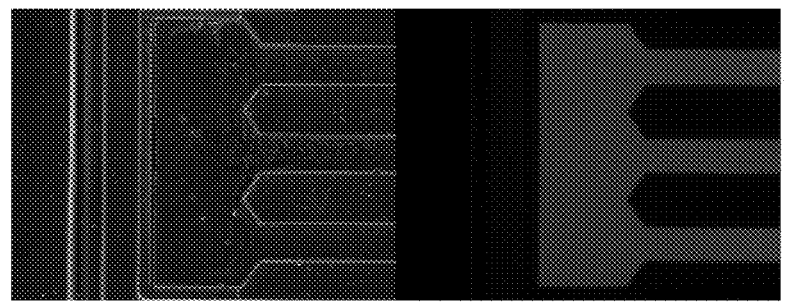

In these embodiments, the invention creates a 3D gel environment for biologic cell culture, for example using a temperature sensitive gel culture matrix, such as Matrigel™, Geltrex™, collagen, etc. An example gel is liquid at 4 C, which, for example polymerizes at room temperature or 37 C. In one example method, cells are initially mixed with a cell suspension on ice. The solution is then pipetted into the cell inlet well, and carried into the microfluidic chamber via capillary flow. In specific examples, the plate is kept at room temperature. The flow rate allows sufficient cell/gel solution to fully fill the culture chamber prior to polymerization. The barrier prevents any of the gel solution from leaking into the flow channel. As the gel warms up, it polymerizes into a solid mass, with cells embedded. Flow of media in the flow channel diffuses into the cell culture chamber (through the gel) and nourishes the cells for long term culture. This novel design allows the invention to provide a 3D gel culture system in a microfluidic device while avoiding the problem of having gel block the flow channels. FIG. 8C illustrates cell/gel loading that operates generally as described above. FIG. 8D illustrates a cell/gel culture with a medium exposed through a perfusion according to specific embodiments of the invention. FIG. 8E illustrates two micrographs showing a culture chamber with an air channel, flow channel, barrier, and cell region according to specific embodiments of the invention. In the right portion, the same region is shown, with a fluorescently labeled gel. Note the gel fully occupies the cell culture chamber but does not extend beyond the barrier.

5. Example Device Operation

Figure 9:
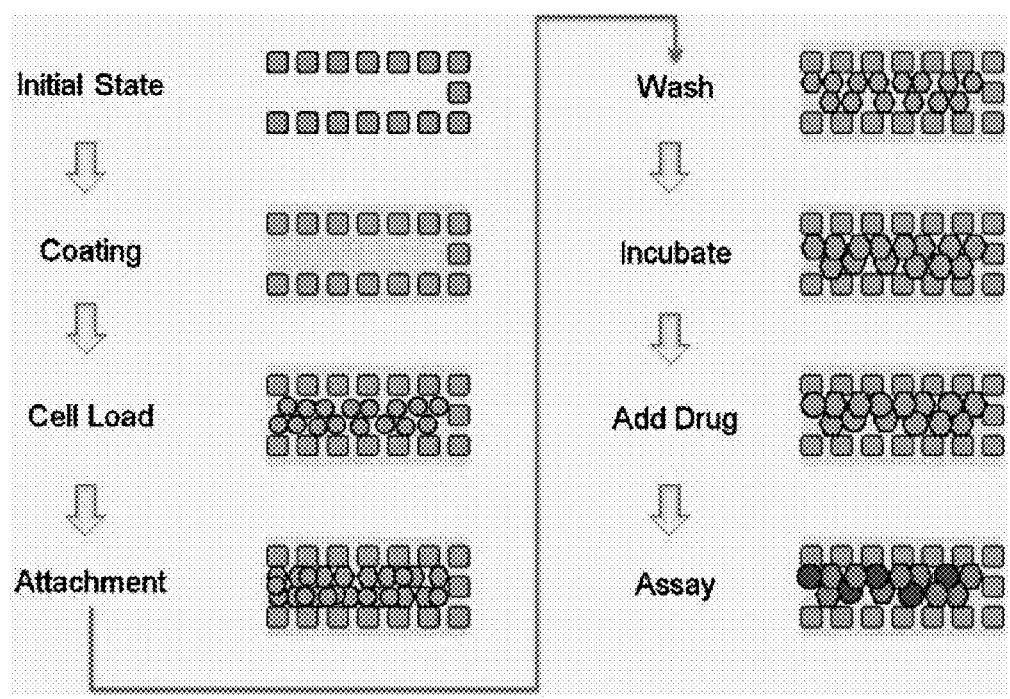
FIG. 9 is a schematic diagram showing steps from an empty culture region to performing a cell assay according to specific embodiments of the invention.

FIG. 9 is a schematic diagram showing steps from an empty culture region to performing a cell assay according to specific embodiments of the invention. Various novel aspects according to specific embodiments of the invention simplify these steps and allow them to be automated.

Cell Loading

Cell loading in specific embodiments of the invention can utilize the rapid surface tension flow between the cell inlet and the flow inlet. In this method, the cell inlet reservoir (upper and lower) is aspirated of its priming solution. Then, the flow inlet upper reservoir is aspirated. An amount (e.g., five microliters) of cell suspension (e.g., trypsinized HeLa human cancer cell line, $5 \times 10^5$ cells/ml) is dispensed into the cell inlet lower reservoir. The flow inlet lower reservoir is aspirated, causing liquid to flow from cell inlet to flow inlet via surface tension/capillary force. Cell loading in various configurations can be completed in approximately 2-5 minutes. The cell loading reservoir is then washed with medium (e.g., Dulbecco's Modified Eagle's Medium, DMEM) and filled with e.g., 50-100 microliters of clean medium. At this state, the plate is was placed in a controlled culture environment for a period (e.g., 37 C, 5% $CO_2$ incubator for 2-4 hours) to allow for cell attachment. As stated above, all dimensions and values are given for illustrative purposes.

3D Gel System

In one example system, referred to at times herein as the 3D:M, multiplexed perfusion imaging of cells can be performed in a 3D gel matrix. An example plate contains 24 independent culture units that can be loaded with cells/gel as a user chooses. In an example system, each row of the plate (A-H) contains 3 fully independent flow units (4 wells each), consisting of a medium inlet (e.g., cols. 1, 5, 9), a cell culture/imaging well (e.g., cols. 2, 6, 10), cell/gel inlet (cols. 3, 7, 10), and an outlet (cols 4, 8, 12). Air diffusion channels (blue) provide gas transfer to the cells. The inlets are designed to allow continuous flow of culture media to the cells at 40 μl/day via a gravity driven process. In this example, each chamber is 1.5×0.5 mm in size, with a height of 200 μm. The perfusion bather (green) ensures uniform nutrient transfer through the gel matrix and a thin cover glass bottom (170 μm) allows for optimum image quality.

3D Gel Loading

Two example operations of 3D microfluidic cell culture according to specific embodiments of the invention are provided below. In a cells embedded method (using a medium such as BD Matrigel), the procedure is as follows: (1) Prepare a cell suspension of 1-5·106 cells/ml, depending on the desired cell number for culture. Optionally, for improved results, resuspend in culture medium on ice. (2) Mix cell suspension with Matrigel on ice. A 1:1 ratio is recommended, but various dilutions are suitable depending on desired gel density. Keep on ice until loaded into the microfluidic plate. (3) Aspirate the flow inlet, cell/gel inlet, and flow outlet wells. Generally, it is desired to empty the liquid from the holes at the bottom of the wells. Over aspiration is preferable avoided, as this may introduce air bubbles. (4) Pipet 5-10 μl of cell/gel mixture into the cell/gel inlet well, generally keeping the plate at room temperature. Once the cell/gel mixture is pipetted into the cell/gel inlet hole, capillary flow will rapidly transport the liquid into the culture chamber, while the perfusion barrier prevents the cells/gel from leaking into the flow channel. (5) In an example embodiment, after ~2 minutes at room temperature, the cells will stop flowing as the gel begins to polymerize. Optionally, polymerization may be completed by, for example, placing in a 37° C. incubator for 15 minutes. (6) Pipet 300 μl of culture medium to the "Flow Inlet" well. This will initiate gravity driven perfusion towards the flow outlet at a rate of about 40 μl/day. The flow channel passes next to the cell culture chamber, and feeds the cells via diffusion as described above. The minimum barrier dimension is 2 micron, allowing soluble factors to freely pass through. Diffusion across the culture chamber occurs in ~20 minutes. (7) For long term culture, refill the flow inlet and empty the flow outlet at an appropriate interval, e.g., every 3 days.

Gel Overlay Method

In an alternative method, a cell suspension may be loaded into the plate without gel and the gel can be overlaid immediately, after cell adhesion, or following a few days of growth. Overlay gel is placed following steps 3 and 4 above using a gel solution (with no cells). The gel will flow over the cells and polymerize in the chamber.

6. Culture Units in Multi-Well Plates

As discussed elsewhere herein, any of the various novel microfluidic cell culture chambers and associated microfluidic structures can, according to specific embodiments of the invention, be integrated with a well titer plate device as is commonly used in macro cell culturing assays. A number of specific examples are provided below, though the invention encompasses other systems for integrating with the microfluidic devices.

Figure 10:
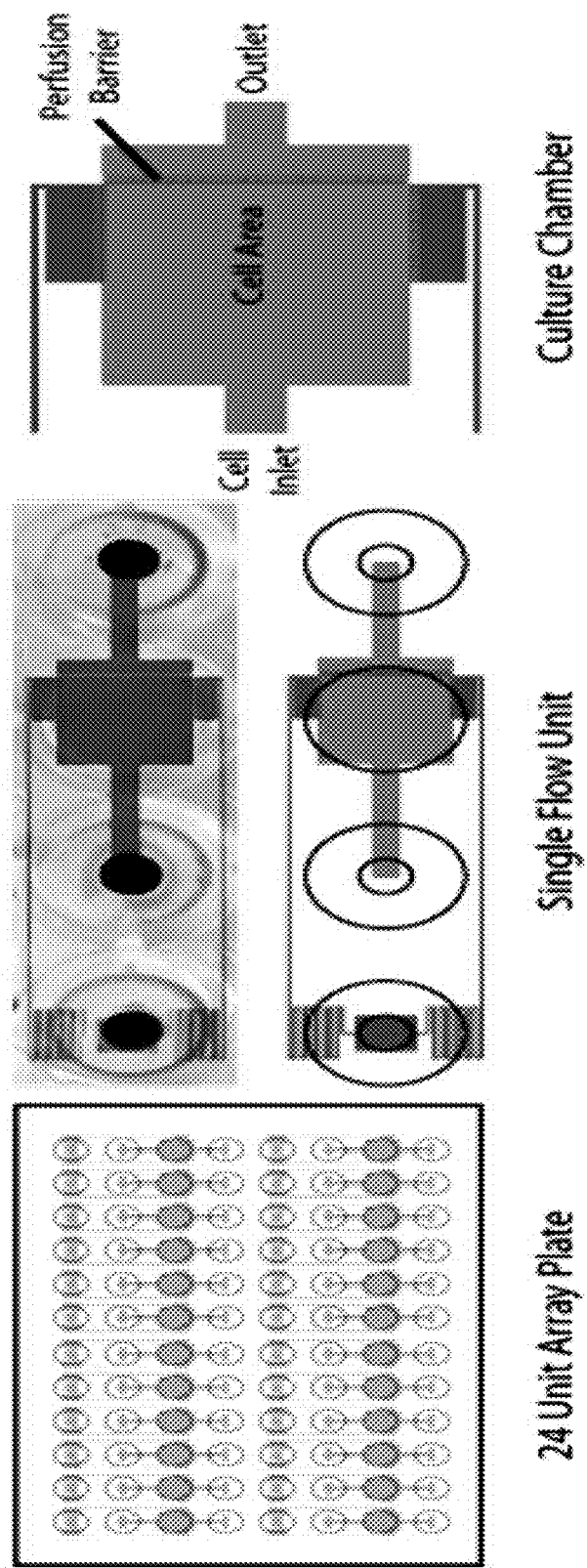
FIG. 10 illustrates a layout of another type of cell culture array designed for general cell culture automation according to specific embodiments of the invention.

FIG. 10 illustrates a layout of another type of cell culture array designed for general cell culture automation according to specific embodiments of the invention. In this design, each culture unit consists of 4 well positions. The first well is for perfusion medium, the second well is for cell inlet, the third well is for imaging the microfluidic chamber, and the fourth well is the outlet. A cell barrier/perfusion channel localizes cells to the cell area and improves nutrient transport during continuous perfusion culture. The low fluidic resistance of the cell inlet to outlet path enables cells to be rapidly loaded via gravity or surface tension methods without an external cell loading mechanism. The high fluidic resistance of the perfusion inlet flow channels allows long term continuous perfusion of medium via gravity flow without any external pump mechanism.

FIG. 11A-D illustrate a 24 unit "3D culture" plate on a 96 well plate according to specific embodiments of the invention. According to specific embodiments of the invention, this configuration is a designed for high-thru-put production work. The design allows cells to be cultured in various 3D gel matrix media with continuous perfusion medium exposure for long term cell assay and cell imaging experiments. In a specific embodiment, using a standard 96-well format and passive gravity driven perfusion allows simple integration with existing laboratory equipment.

Figure 11A:
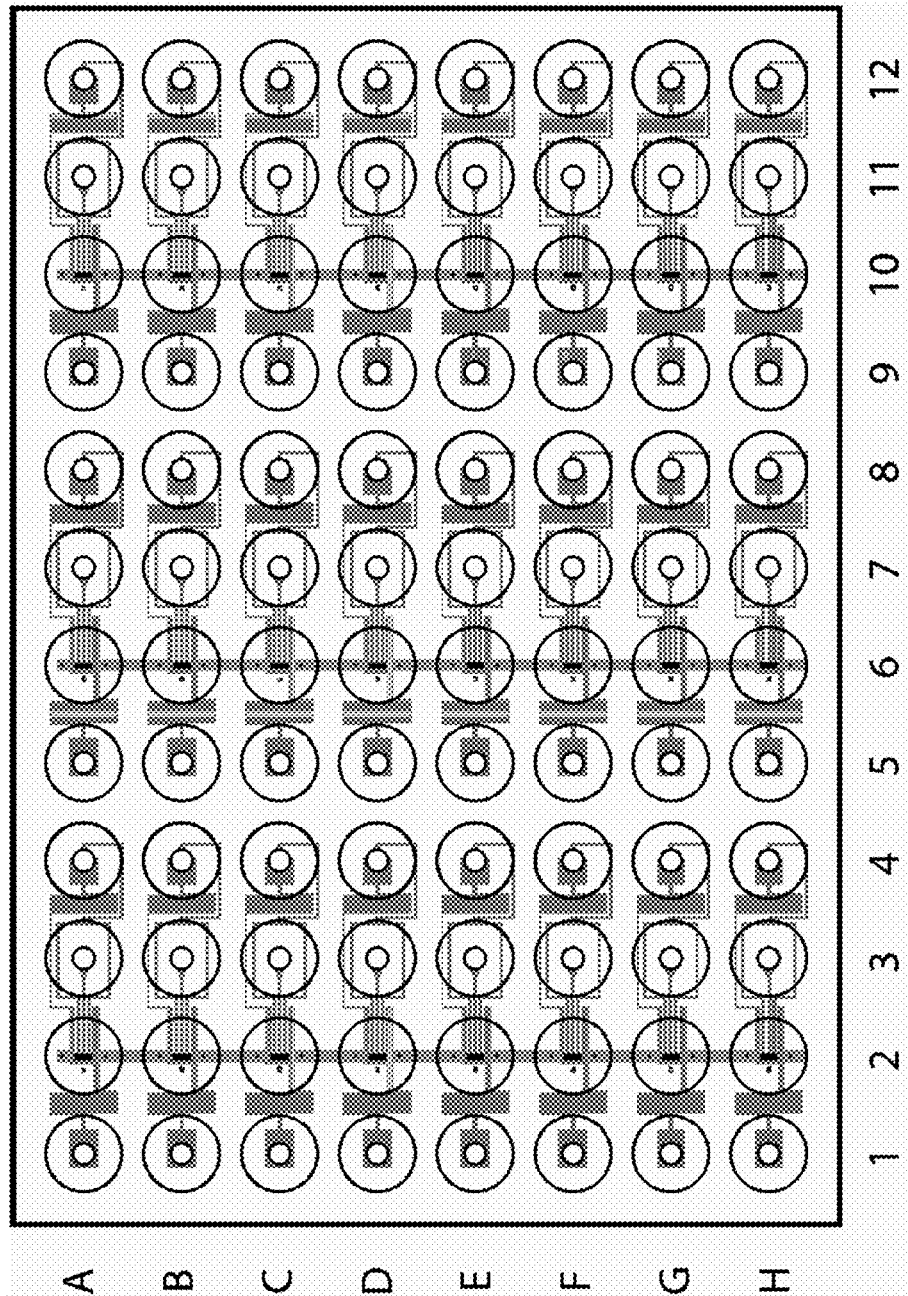
FIG. 11 A-D illustrate a 24 unit "3D culture" plate on a 96 well plate according to specific embodiments of the invention.
Figure 11B:
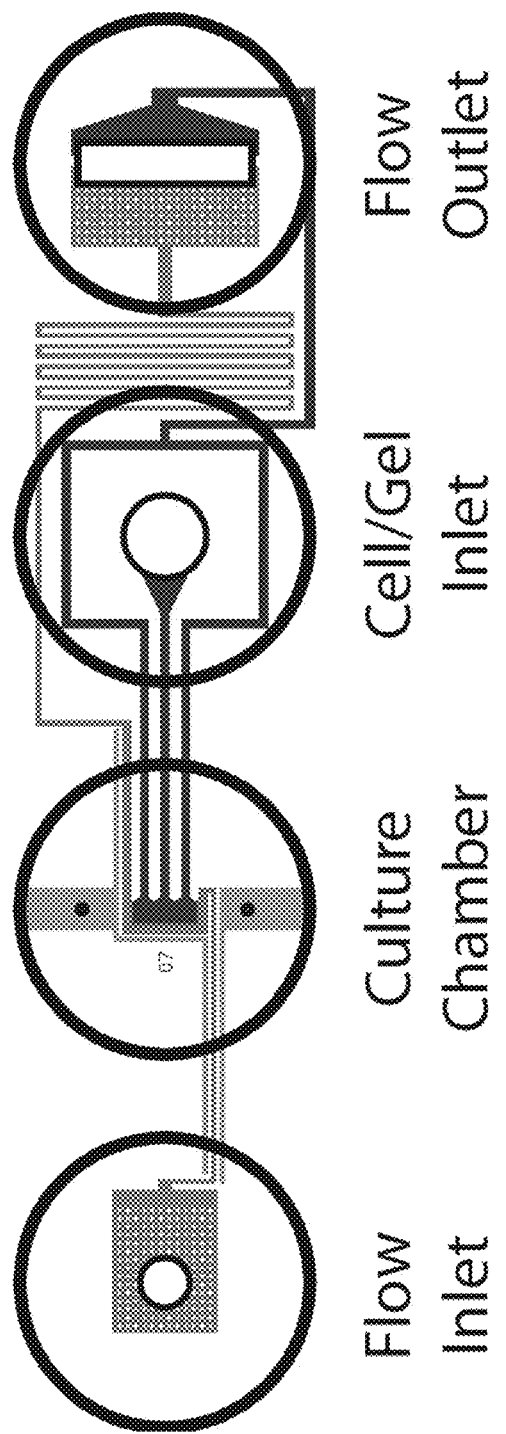
Figure 11C:
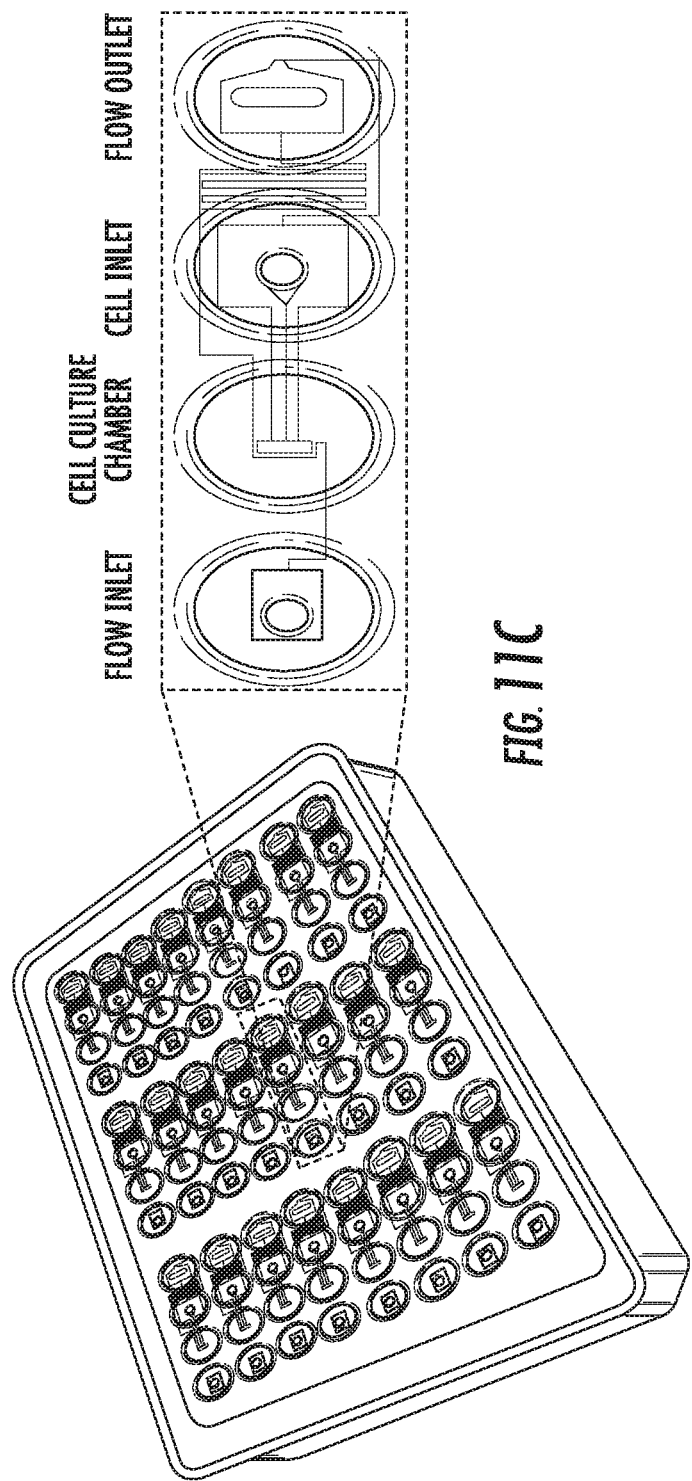
Figure 11D:
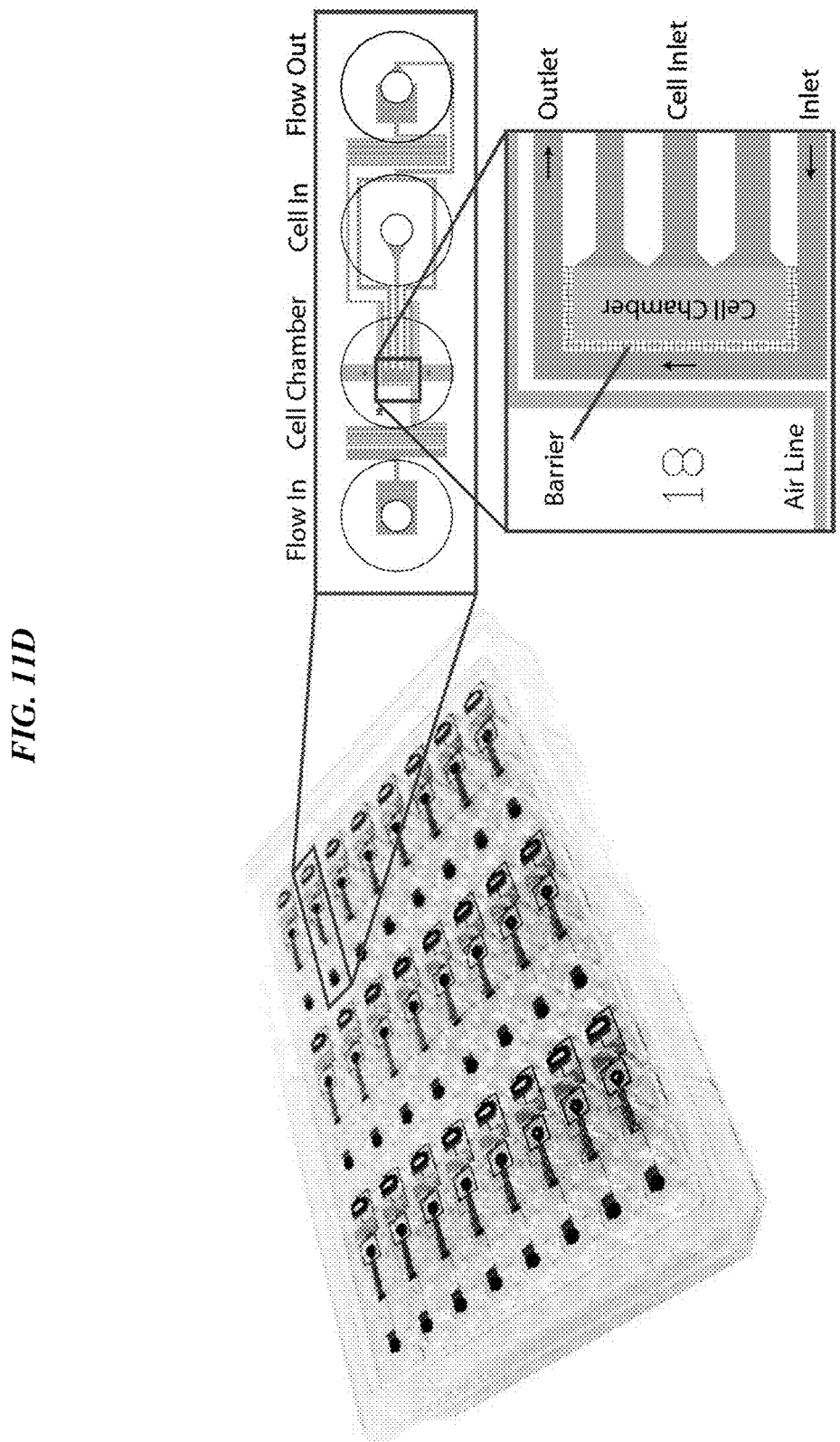

In a specific example, a 96-well plate contains 24 independent 3D culture units with microfluidic channels (which are stained in the Figure for visibility) A single unit with flow channels stained is shown in FIG. 11C. In an example operation, media flows from the inlet well past the cultured cells and collects in the outlet well. Cells and gel are loaded by the user into the biomimetic cell culture chamber.

In an example specific system, the cell chamber is designed to mimic the interstitial tissue environment, with cells embedded or overlayed in physiologic extracellular matrix (ECM), and fed via diffusion from a continuously perfused capillary channel. The cell microenvironment enables long term growth in, e.g., a 200 micron thick gel layer. Oxygenation channels maintain adequate gas transport, and the glass coverslide bottom allows high quality cell imaging. The standard layout allows the advanced microfluidic units to be operated just like a typical 96-well plate. The gravity driven perfusion design eliminates the need for pump or tubing connections, as described above.

In an example system, an expected number of cells per unit is about 500 cells. An example perfusion rate is 40 ul/day for a single unit. The cell chamber volume is 150 nL, and the chamber dimensions are 1.5×0.5×0.2 mm. The gas diffusion membrane is 50 um silicone with a bottom surface #1.5 thickness coverglass.

7. Open Chamber Microfluidic Perfusion Plate for Cell Culture

In many microfluidic systems, cells generally must be introduced to the culture chamber via flow from a cell inlet well. This can hamper use of such devices for cultures that need to introduce large cells, cell clusters, or tissue samples that do not transport well in microchannels. In a typical existing open top well (e.g. 384 or 1586 well plate), cell seeding is easy, but there is no way to maintain a continuous flow environment to the cells.

An open top microfluidic cell culture chamber for continuous perfusion according to specific embodiments uses the surface tension of liquid in the open chamber to counteract flow pressure, thereby preventing liquid from spilling out of the open chamber and instead flowing to downstream channels. In this aspect, embodiments allow the combination of cell introduction into an open well and integrated microfluidic perfusion control.

Figure 12:
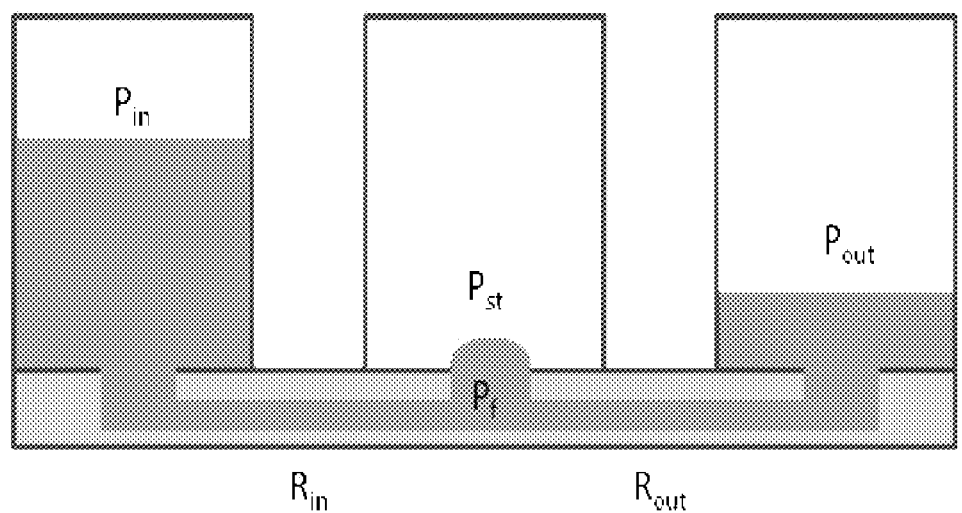
FIG. 12 is a schematic diagram illustrating fluidic operation of open top cell culture systems according to specific embodiments of the invention.

An important aspect of the operation of open top systems according to specific embodiments of the invention is illustrated in FIG. 12. Fluid mechanics dictates that liquid will move from regions of high pressure to lower pressure. Pressure differences can be caused by gravity (difference in liquid level), applied pressure (from pumps), or surface tension. According to specific embodiments of the invention, an open top cell culture chamber is provided such that the surface tension pressure of the liquid above the open well is higher than the chamber pressure, creating a surface tension barrier that prevents liquid from flowing up out of the open chamber. In the figure, the angle of the fluid surface above the chamber walls is exaggerated for illustration purposes.

In the example shown in the schematic of FIG. 12, $P_{in}$, $P_{st}$, $P_f$, $P_{out}$ are the pressures at the inlet well ($P_{in}$), above the open chamber ($P_{st}$), inside the culture chamber ($P_f$), and at the outlet well ($P_{out}$). $R_{in}$, $R_{out}$ are the fluidic resistances between the inlet well and chamber, and between the chamber and outlet well. When $P_{st} > P_f$, and $P_{in} > P_f > P_{out}$; then liquid flows from the inlet well to the outlet well with no flow escaping the chamber into the middle well. The surface tension force is $P_{st} = 2\gamma/R$ (Young's equation). In a typical water/plastic situation for a 2 mm diameter chamber, this is approximately 140 Pa. Gravity pressure from a 1 cm head (height of standard 96 well plate) is ~100 Pa (not enough to overcome surface tension). By the "Ohm's Law" relation, when $P_{in} > P_{out}$; $P_f = (P_{in} - P_{out}) * (R_{out}/(R_{out} + R_{in})) + P_{out}$. This means that if $R_{in}$ is large in relation to total resistance, a large amount of pressure can be applied to the inlet well without creating a large pressure at the chamber. In one example design according to specific embodiments, resistances are such that when 1 atm is applied to the inlet well, the chamber only experiences ~50 Pa pressure, not enough to overcome the surface tension force.

Passive Array Plate

Figure 13A:
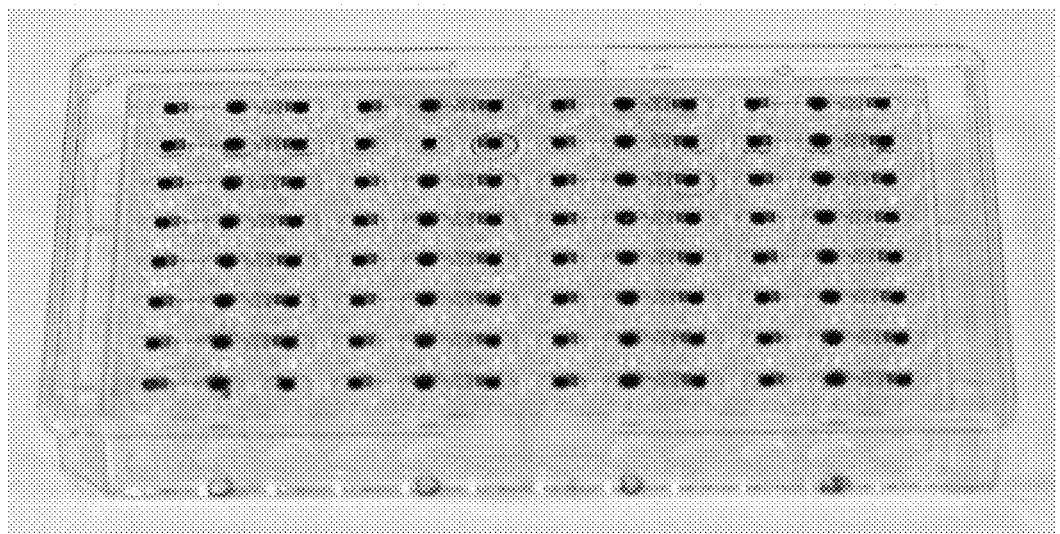
FIG. 13 is an illustration of an example 96 well plate having 32 perfusion units with a dye in the culture medium for illustrative purposes according to specific embodiments of the invention: (A) shows an entire 96-well plate; (B) shows a close up illustration of a 3-well perfusion unit view from the top (from the opening of the cell to the open top culture chamber), (C) shows a close up illustration of a 3-well perfusion unit view from the bottom to more clearly see the microfluidic structures as described herein which are stained for easier viewing.
Figure 13B:
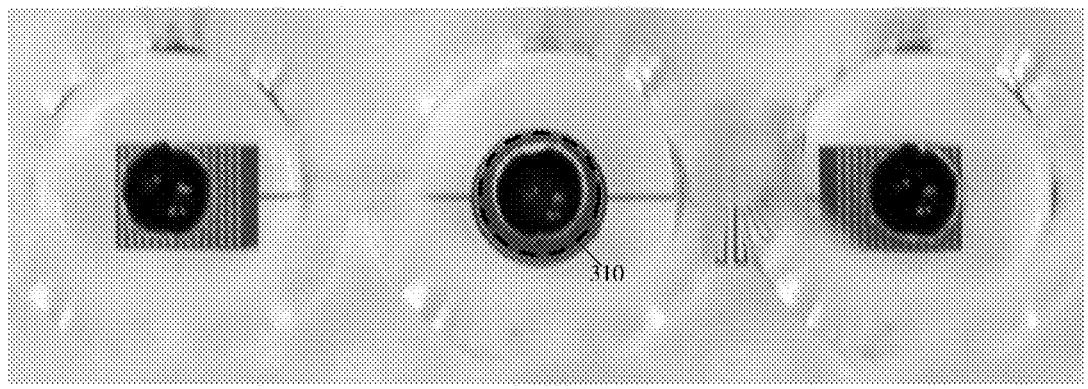

One example implementation of embodiments according to the open top aspect is a cell culture array on a standard 96-well plate, where each unit consists of 3 well positions: a flow inlet well, an open top chamber, and a flow outlet well. (It will be understood that in various embodiments, plates with larger or smaller numbers of wells or units that have more or less than 3-wells may embody the invention.) FIG. 13 is an illustration of an example 96 well plate having 32 perfusion units with a dye in the culture medium for illustrative purposes according to specific embodiments of the invention FIG. 13B shows a top view of a single perfusion unit in an example system. The left well is the inlet, the center is the open culture chamber, and the right well is the outlet. A 2 mm open top 310 of the culture chamber is indicated by the dashed circle.

Figure 13C:
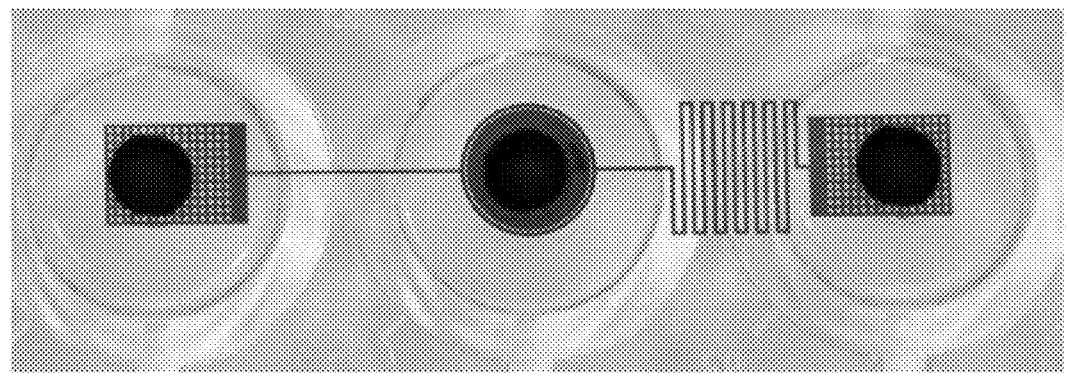

FIG. 13C Illustrates a bottom view of a single example perfusion unit. The serpentine channels shown at the right control the gravity perfusion rate to be, in one example, approximately 100 microliters/day.

Figure 14:
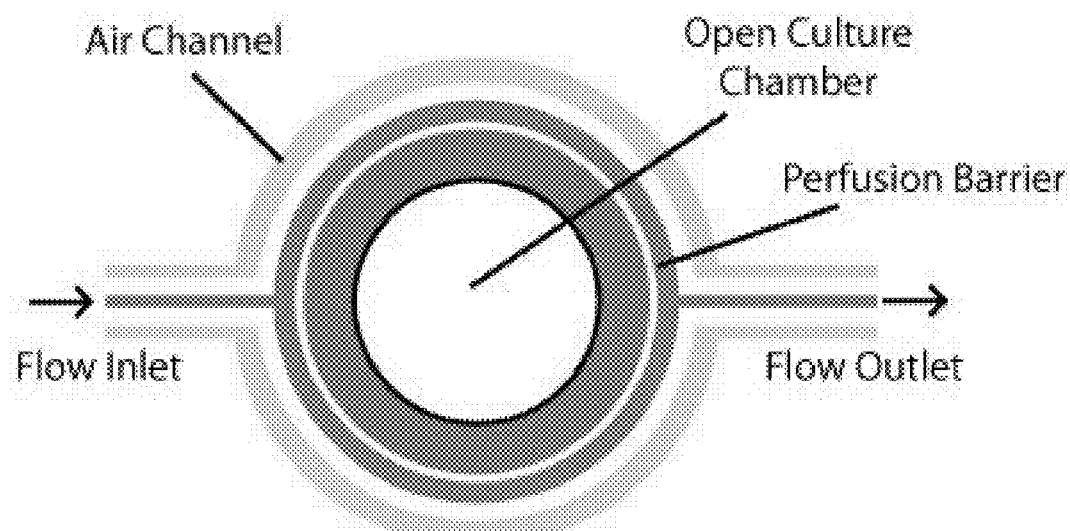
FIG. 14 is a top view schematic illustration of an example design of an open top perfusion chamber according to specific embodiments of the invention. In this example, a 2 mm hole (white) is cut into 3 mm microfluidic chamber (orange). A narrow perfusion bather (green) surrounds the culture chamber to separate flows from cells. An outer air channel (blue) oxygenates the medium in the flow channels (gray).
Figure 15:
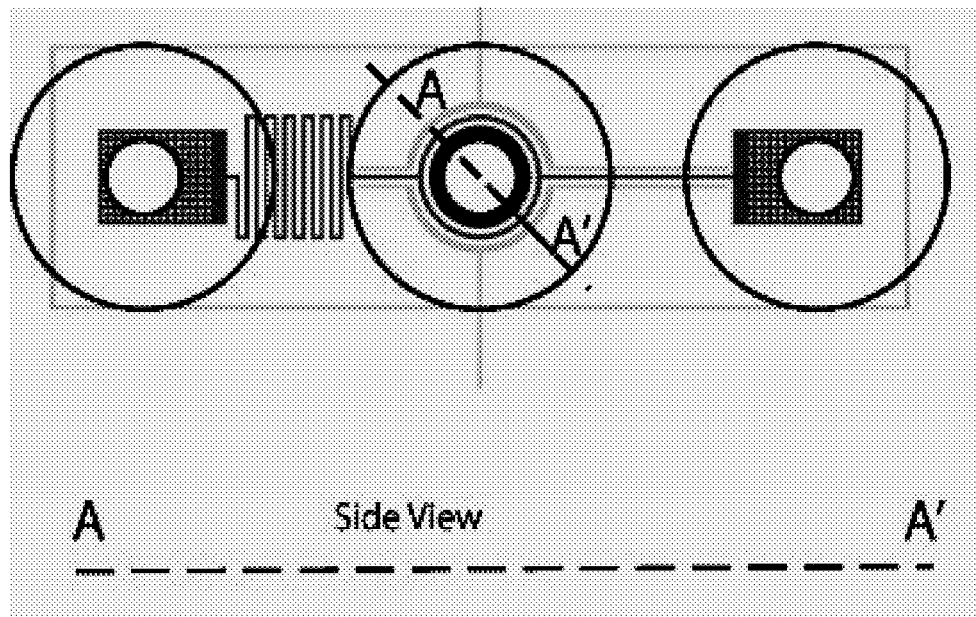
FIG. 15 is a top view schematic illustration of an example perfusion unit according to the invention and a cross section side view schematic of an example design of an open top perfusion chamber showing representative layers.
Figure 15:
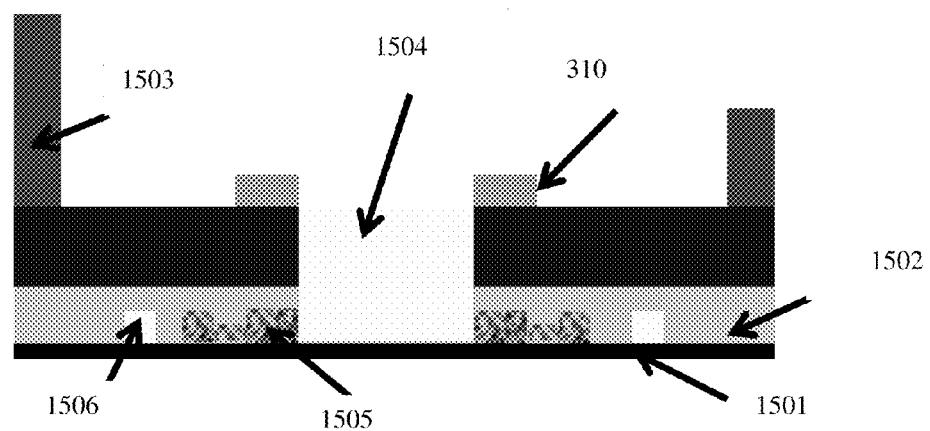

FIG. 14 is a top view schematic illustration of an example design of an open top perfusion chamber according to specific embodiments of the invention. In this example, a 2 mm hole (white) is cut into 3 mm microfluidic chamber (orange). A narrow perfusion barrier (green) surrounds the culture chamber to separate flows from cells. An outer air channel (blue) oxygenates the medium in the flow channels (gray). FIG. 15 is a top view schematic illustration of an example perfusion unit according to the invention and a cross section side view schematic of an example design of an open top perfusion chamber showing representative layers. An example open chamber is about 2 mm in diameter with a 1 mm height. FIG. 15 illustrates glass layer 1501, microfluidics layer 1502, well layer 1503, cell culture reservoir 1504, microfluidic channels 1505, teflon ring 310, and air channel 1506.

Figure 16:
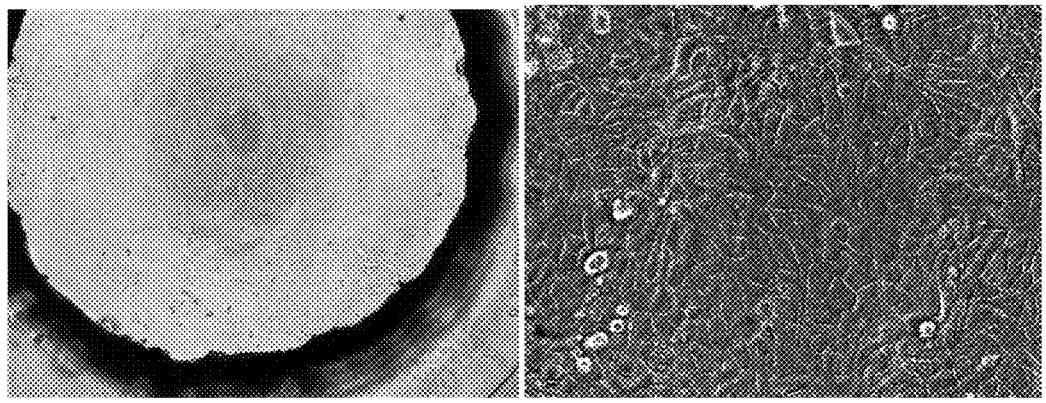
FIG. 16 is a photomicrograph showing a 2D perfusion culture of MCF-10A cells after 7 days. The left side shows cells in relation to the open well. Right shows a magnified view of cells in the culture chamber, demonstrating a confluent monolayer of cells on the bottom surface.
Figure 17:
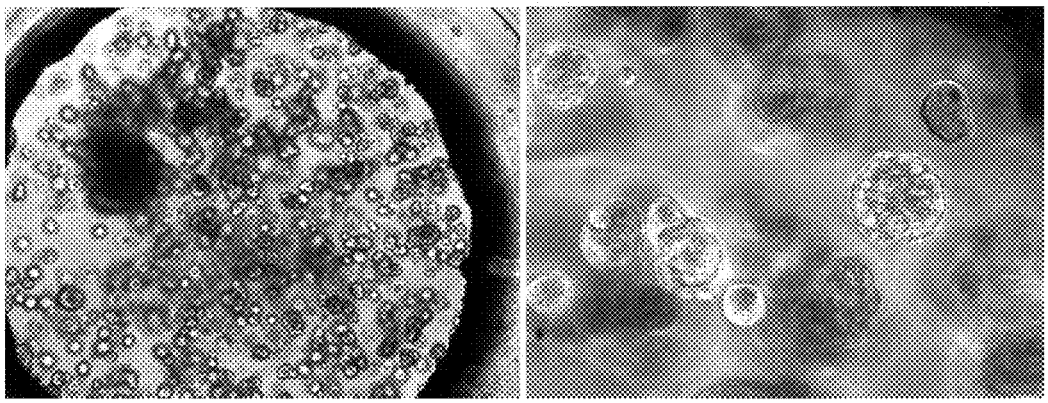
FIG. 17 is a photomicrograph showing a 3D perfusion culture of MCF-10A cells after 7 days. Cells were embedded in BD Matrigel. Left shows cells in relation to the open well. Right shows a magnified view of cells in the culture chamber, demonstrating a clustered 3D aggregate morphology suspended in gel.

This chamber design supports culture of cells in 2D systems using liquid culture medium, as well as 3D cultures as described herein. In 2D culture, cells adhere to the glass floor after being dispensed directly into the culture region. Perfusion of medium passes over the cells for long term growth. In the 3D format, cells are embedded in a gel (such as BD Matrigel), and dispensed into the culture well. The gel will be localized to the central chamber by the perfusion barrier, allowing medium to flow around the gel and diffuse in to feed the cells. FIG. 16 is a photomicrograph showing a 2D perfusion culture of MCF-10A cells after 7 days. The left side shows cells in relation to the open well. Right shows a magnified view of cells in the culture chamber, demonstrating a confluent monolayer of cells on the bottom surface. FIG. 17 is a photomicrograph showing a 3D perfusion culture of MCF-10A cells after 7 days. Cells were embedded in BD Matrigel. Left shows cells in relation to the open well. Right shows a magnified view of cells in the culture chamber, demonstrating a clustered 3D aggregate morphology suspended in gel.

Controlled Perfusion Plate

A second implementation of the open top design is in an active control plate. In this configuration, the open culture chamber is routed to 6 upstream inlet wells, a gravity perfusion well, and an outlet well. The plate can be sealed to a pneumatic manifold, allowing pressure driven control of the 6 inlet solutions. This allows experiments where solutions are quickly changed over the cells. Pressure driven flow of up to 10 PSI is possible due to the large resistance region between the inlet and culture chamber, leading to a pressure near the chamber less than $\frac{1}{1000}^{th}$ the input pressure.

Figure 18:
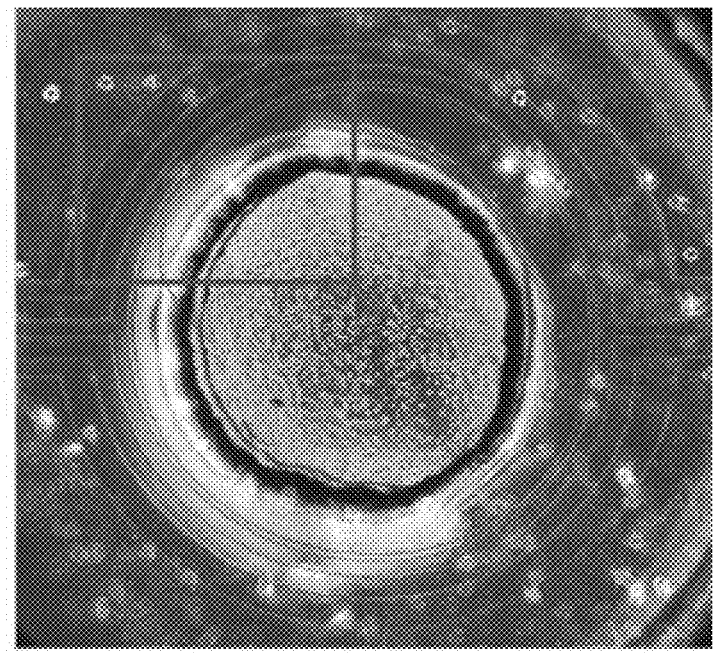
FIG. 18 is a photograph of an open chamber with cells. (Top) and a close up of the channel structure, showing the open cell chamber, perfusion barrier ring, flow channel, and outer air channel (Bottom) according to specific embodiments of the invention.
Figure 18:
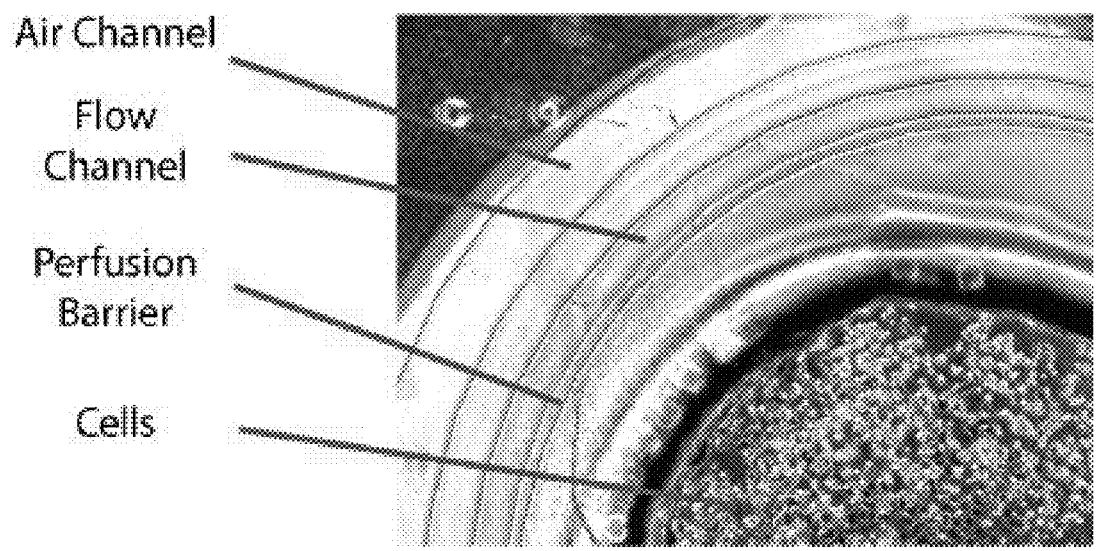

FIG. 18 is a photograph of an open chamber with cells. (Top) and a close up of the channel structure, showing the open cell chamber, perfusion barrier ring, flow channel, and outer air channel (Bottom) according to specific embodiments of the invention.

Figure 19A:
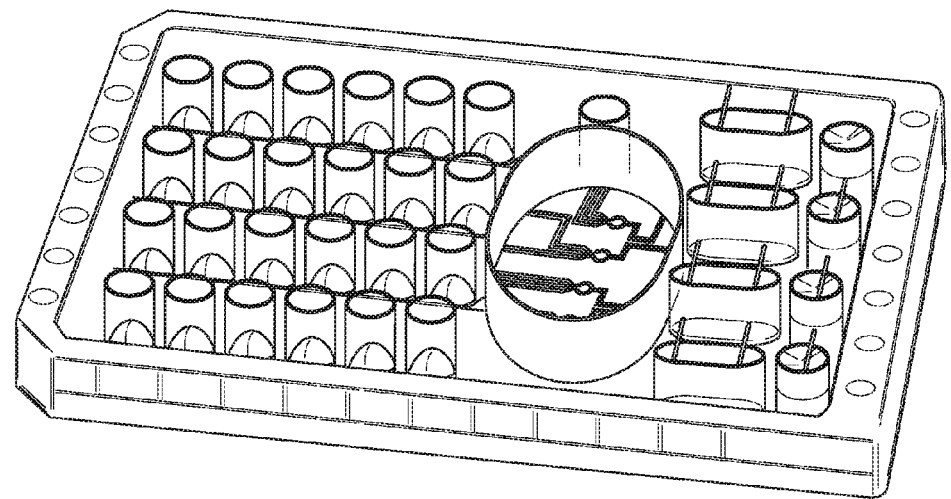
FIG. 19A-B are photographs illustrating an example of an active control plate according to specific embodiments.
Figure 19B:
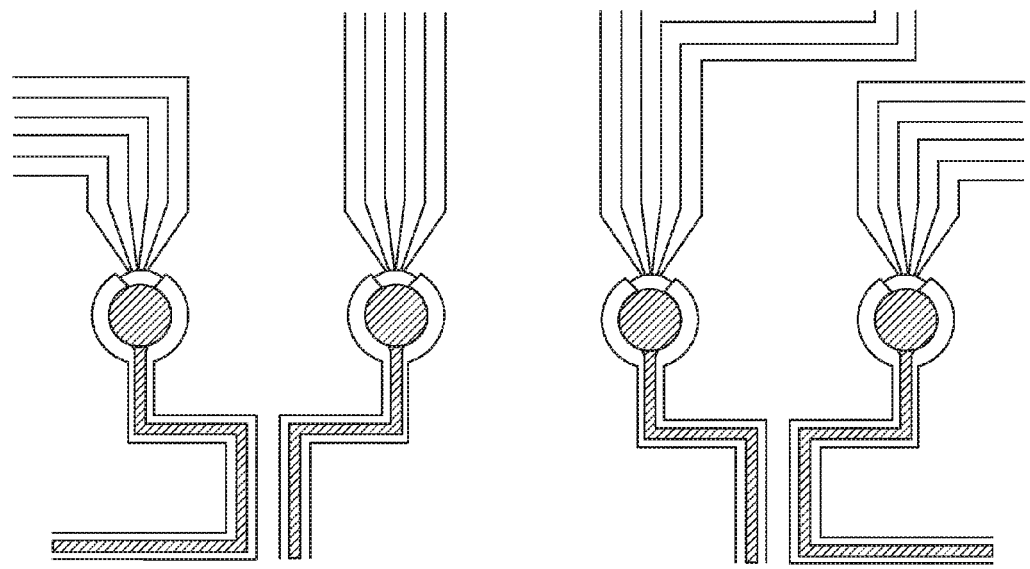

FIG. 19A-B are photographs illustrating an example of an active control plate according to specific embodiments. FIG. 19A shows a plate design with 4 independent flow units (rows of the plate) with 6 inlet solutions, an open chamber, an outlet, and a gravity flow channel. FIG. 19B shows the four open chambers (green circles), with inlet streams above and outlet streams below the open chamber. The design allows flows to pass from the inlet to outlet channels without overflowing the open chamber. The availability of multiple liquid or reagent inlets provides systems that are particularly good for live cell imaging and other experiments and assays in cell biology. In such a system a research can study cultures of pancreatic or other organ cells, or cancer cells, to determine how they respond to different drugs or other stimulus introduced via the inlets. In specific embodiments of this design, a gravity well is also provides to facilitate maintaining (e.g., feeding) the cells before experiments are performed.

Figure 20A:
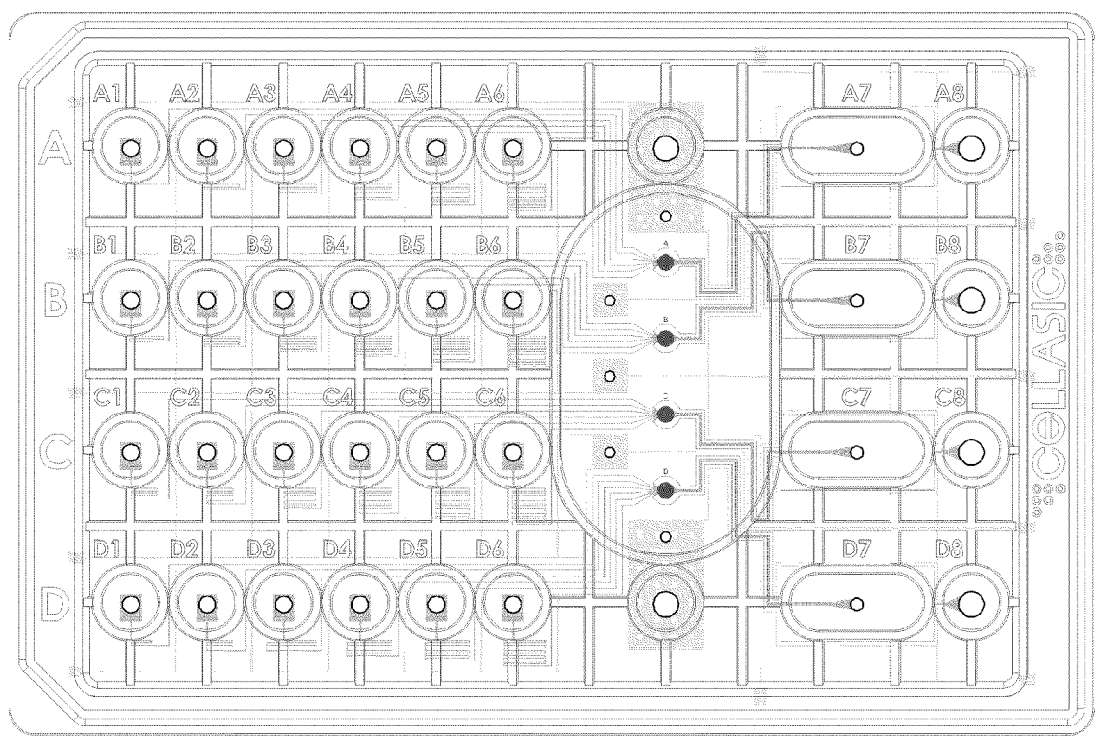
FIG. 20A-B are schematics illustrating an example of an active control plate according to specific embodiments.
Figure 20B:
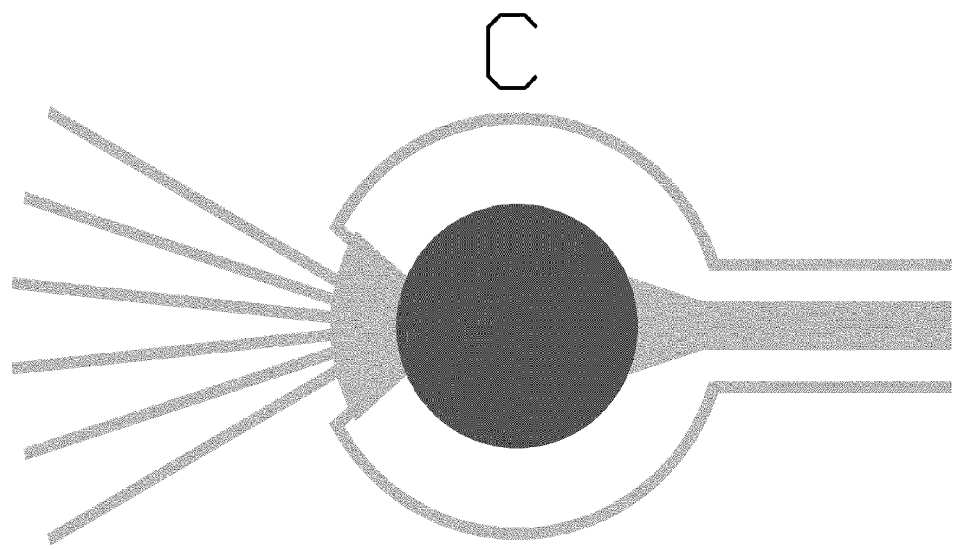

FIG. 20A illustrates the layout of the active control plate with 4 independent units (rows), 6 upstream inlets (A1-A6, B1-B6, C1-C6, D1-D6), the open chambers (red circles) in a central imaging window with four culture chambers, a large outlet well (oval, A7, B7, C7, D7), and gravity perfusion well (last column, A8, B8, C8, D8). FIG. 20AB is a schematic of the culture chamber showing the 6 inlet channels, 2 mm diameter open culture chamber (red), outlet (center right), and gravity feed (top and bottom right).

Figure 21A:
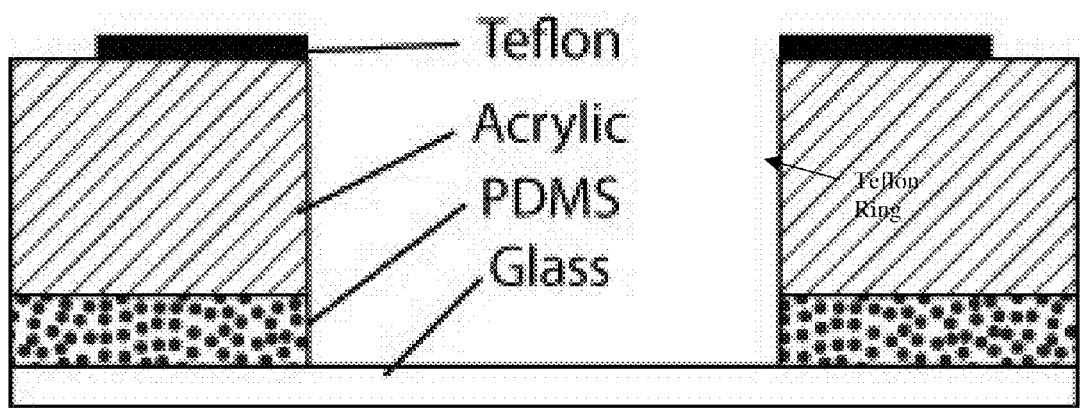
FIG. 21A-B are schematics and a photo illustrating an example of (A) a cross section of the open chamber showing materials used for construction. The bottom layer is a solid glass slide. On top is a layer of molded PDMS containing microfluidic structures as described herein. Also, as described herein, an acrylic sheet is used in the molding process and the PDMS remains attached to it. For the open top cell chamber, in specific embodiments, this acrylic sheet is laser cut, etched, drilled or otherwise opened to create the open top culture chamber. In specific embodiments, a ring of Teflon tape or similar hydrophobic material is placed around the open chamber inside the well to increase the surface tension, for example by preventing wetting of the acrylic. Alternatively, the acrylic may be coated or treated or fabricated to have a higher hydrophobicity. The open chamber is laser cut in these three layers (prior to attaching the glass bottom) and (B) a photograph showing the Teflon ring on the top surface of the device. Clear liquid is filled in the open chamber, with microchannels filled with red dye.
Figure 21B:
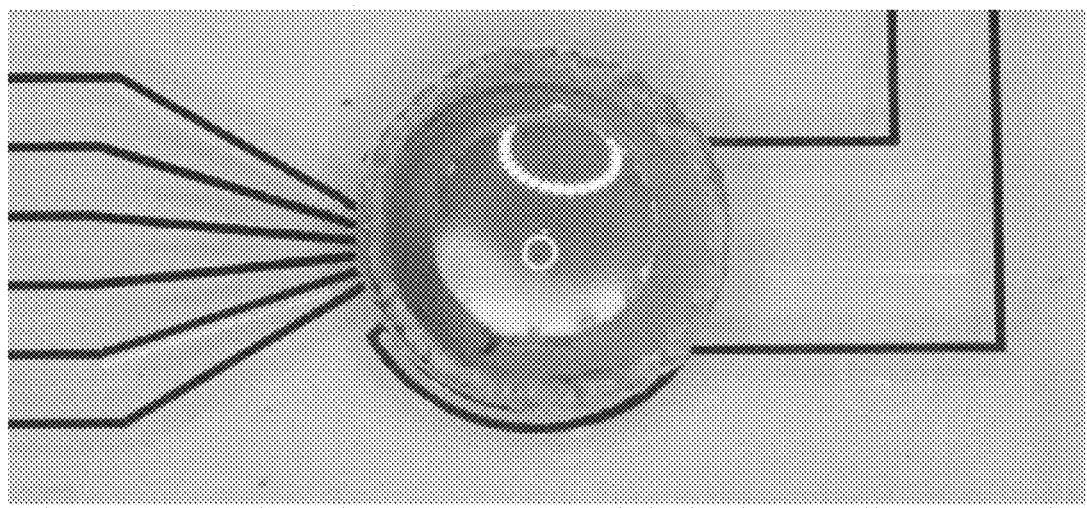

FIG. 21A-B are schematics and a photo illustrating an example of (A) a cross section of the open chamber showing materials used for construction. The bottom layer is a solid glass slide. On top is a layer of molded PDMS containing microfluidic structures as described herein. Also, as described herein, an acrylic sheet is used in the molding process and the PDMS remains attached to it. For the open top cell chamber, in specific embodiments, this acrylic sheet is laser cut, etched, drilled or otherwise opened to create the open top culture chamber. In specific embodiments, a ring of Teflon tape or similar hydrophobic material is placed around the open chamber inside the well to increase the surface tension, for example by preventing wetting of the acrylic. Alternatively, the acrylic may be coated or treated or fabricated to have a higher hydrophobicity. The open chamber is laser cut in these three layers (prior to attaching the glass bottom) and (B) a photograph showing the Teflon ring on the top surface of the device. Clear liquid is filled in the open chamber, with microchannels filled with red dye. The Teflon ring, for example, increases the hydrophobicity of the top surface. This increases the surface tension and prevents liquid from spilling out of the culture chamber. In an example embodiment, the Teflon is applied during fabrication of the bottom acrylic portion of the plate. A strip of Teflon is taped onto the acrylic sheet before laser cutting. The laser cutter creates the open chamber by cutting through the PDMS, acrylic, and Teflon at the same time. The laser cutter also preferably cuts the excess Teflon tape around the outside of the cell chamber opening to create the circular ring. The end result is a Teflon ring that is a roughly donut shape with 1 mm width and 200 micron thickness. Cutting off the excess Teflon or otherwise restricting the hydrophobic treatment of the acrylic to the area just around the culture chamber can facilitate subsequent joining of the acrylic bottom to an open bottom well plate. Since cell culture media is hydrophilic, a surface that is hydrophilic will prevent the liquid from flowing out of the well. Telfon is an extremely hydrophobic material with a water contact angle around 120 degrees. Without the Teflon, there is a liquid/air/acrylic interface, which is less hydrophobic, and more likely to overflow during experiment.

It will be understood that other configurations that allow for an open top culture area are possible. In one example, the holes through the acrylic may be drilled so that there is a sunken edge around the culture chamber hole and that sunken edge can be treated to be hydrophobic while leaving the surface that attaches to the well portion untreated.

8. Pneumatic Manifold

While gravity or passive loading is effective for some microfluidic cell culture devices, in some embodiments, a proprietary pneumatic manifold, as described herein, is mated to the plate and pneumatic pressure is applied to the cell inlet area for cell loading. For particular cell systems, it has been found that overall cell culture area design can be made more effective when it is not necessary to allow for passive cell loading.

Figure 22A:
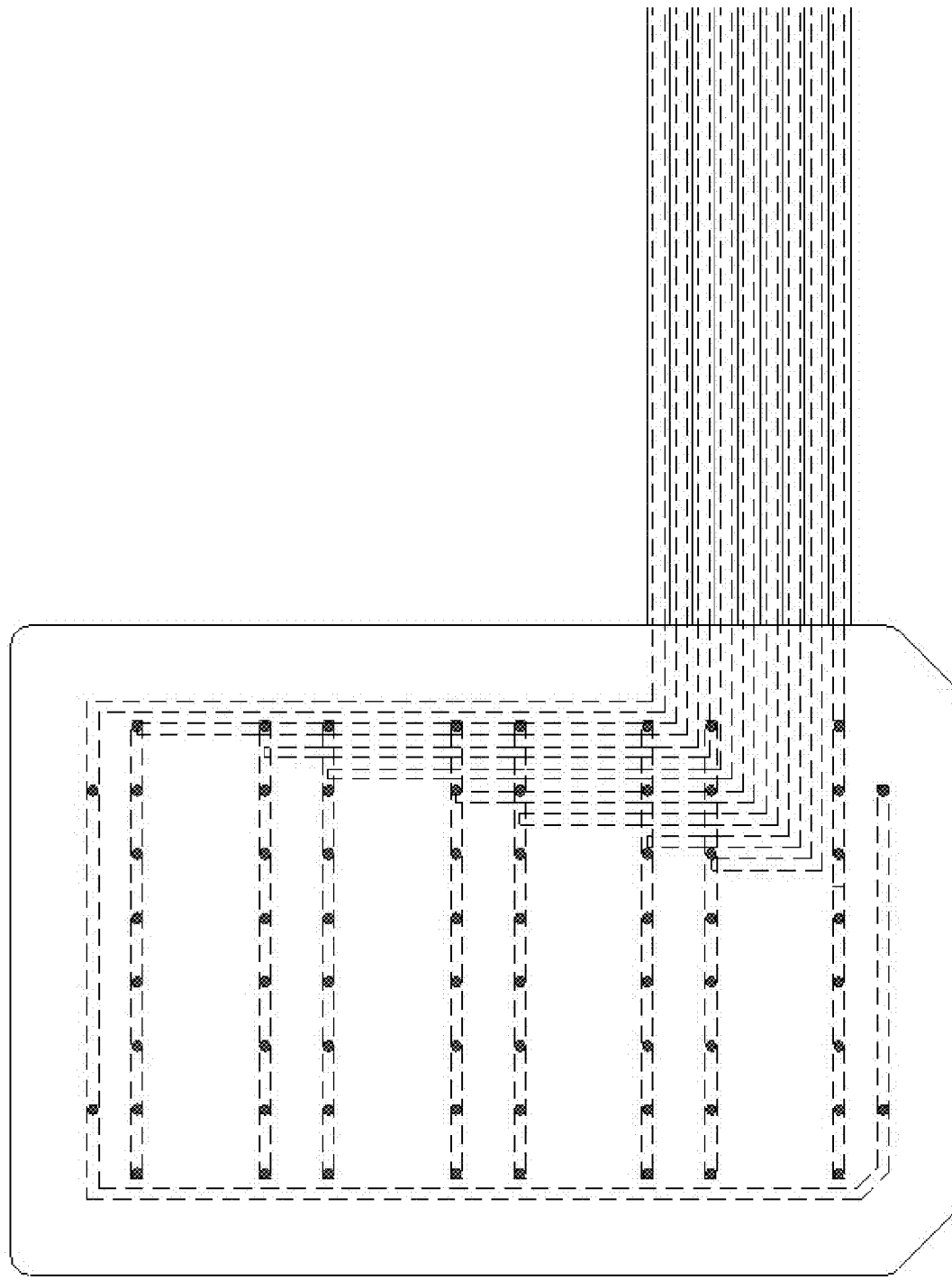
FIG. 22A-C shows a top view, side view, and plan view of a schematic of an example manifold according to specific embodiments of the invention. In this example, the eight tubing lines to the right are for compressed air, and each is configured to provide pressure to a column of cell inlet wells in a microfluidic array. The left-most line in the figure is for vacuum and connects to an outer vacuum ring around the manifold. Each column of wells is generally connected to a single pressure line with wells above imaging regions skipped.
Figure 22B:
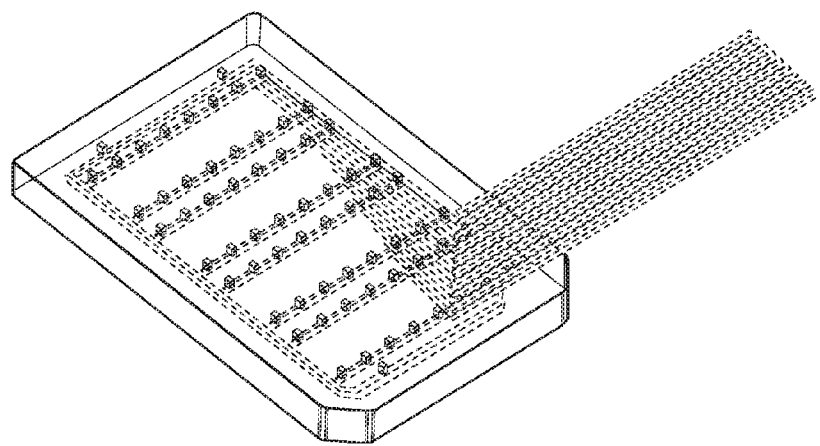
Figure 22C:

FIG. 22A-C shows a top view, side view, and plan view of a schematic of an example manifold according to specific embodiments of the invention. In this example, the eight tubing lines to the right are for compressed air, and each is configured to provide pressure to a column of cell inlet wells in a microfluidic array. The left-most line in the figure is for vacuum and connects to an outer vacuum ring around the manifold. Each column of wells is generally connected to a single pressure line with wells above imaging regions skipped. The manifold is placed on top of a standard well plate. A rubber gasket lies between the plate and manifold, with holes matching the manifold (not shown). The vacuum line creates a vacuum in the cavities between the wells, holding the plate and manifold together. Pressure is applied to the wells to drive liquid into the microfluidic channels (not shown). A typical pressure of 1 psi is used, therefore the vacuum strength is sufficient to maintain an air-tight seal. In one example there are 9 tubing lines to the pressure controller:

8 lines are for compressed air and 1 line is for vacuum (leftmost). In specific example embodiments, each column is connected to a single pressure line. Columns above the cell imaging regions are skipped.

Pressurized cell loading in a system according to specific embodiments of the invention has been found to be particularly effective in preparing cultures of aggregating cells (e.g., solid tumor, liver, muscle, etc.). Pressurized cell loading also allows structures with elongated culture regions to be effectively loaded. Use of a pressurized manifold for cell loading and passive flow for perfusion operations allows the invention to utilize a fairly simple two inlet design, without the need for additional inlet wells and/or valves as used in other designs.

Modified Manifold

In a further embodiment, a plate manifold includes an additional "gas line" that is used to bathe the cells in the microfluidic device with a specified gas environment (for example, 5% $CO_2$). Other examples include oxygen and nitrogen control, but any gaseous mixture can be sent to the cells. The gas flows through the manifold into the sealed wells above the cell culture area and holes in the microfluidic device enable the gas to flow into specified microfluidic air channels, as described above. The gas permeable device layer (PDMS) allows the gas to diffuse into the culture medium prior to exposing the cells. By continuously flowing the gas through the microfluidic plate, a stable gas environment is maintained.

This provides an optional means for controlling the gas environment to placing the microfluidic plate into an incubator. In this modified manifold, the manifold can be used to create a "micro-incubator" independent of the ambient air.

Figure 23:
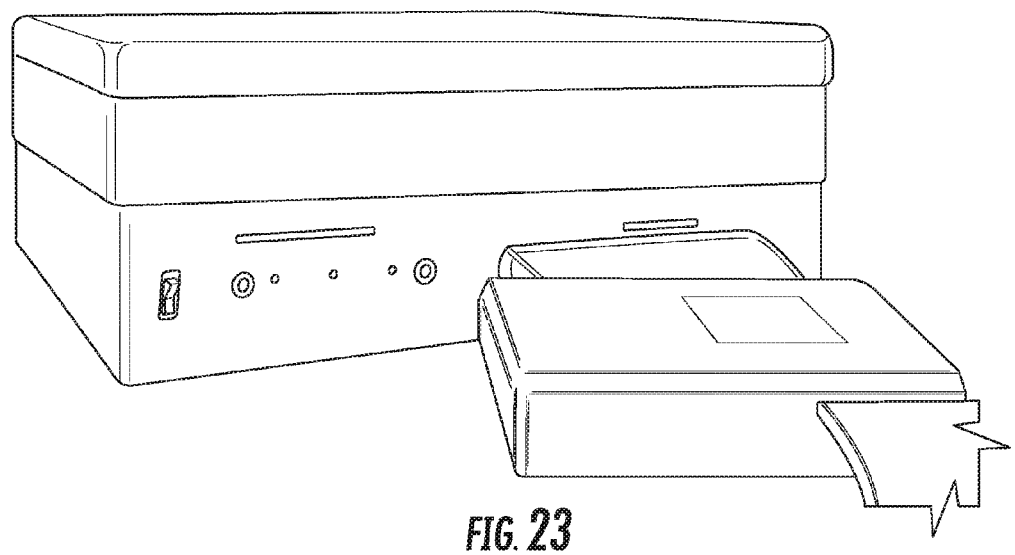
FIG. 23 illustrates an example system and manifold for operating the microfluidic plates according to specific embodiments of the invention.
Figure 24:
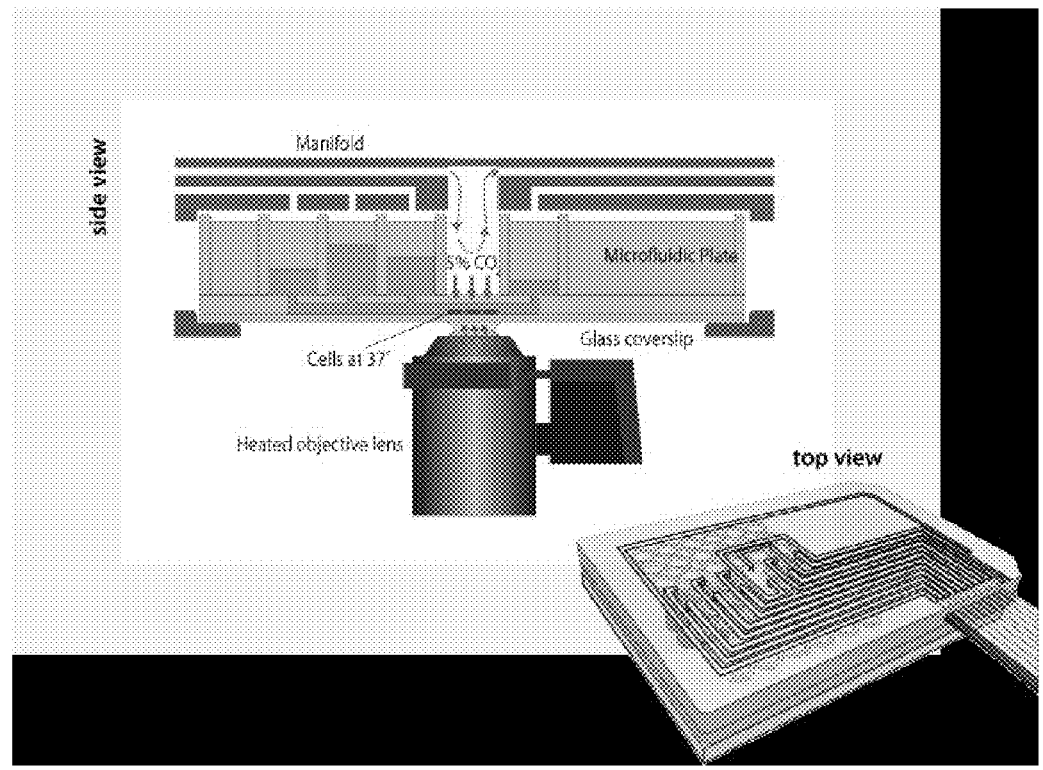
FIG. 24 illustrates a manifold with additional gas line and an objective lens according to specific embodiments of the invention.

FIG. 23 illustrates an example system and manifold for operating the microfluidic plates according to specific embodiments of the invention.

Fluid Flow and Operation: Gravity and Surface Tension Flow

The format of the microfluidic plate design allows two automation-friendly flow modalities dependent on the extent of dispensing/aspiration. The first is surface tension mediated flow. In this case, when the lower reservoir is aspirated in either one of the wells, the capillary force of the fluid/air interface along with the wetted surfaces (glass, silicone, acrylic) will rapidly draw liquid in from the opposing well until the lower reservoir is filled (or in equilibrium with the opposing lower reservoir). This effect is useful for microfluidic flows as it is only evident when the reservoir diameter is small and the flow volumes are small. In an example array design, the lower reservoir wells are 1-2 mm in diameter, and with a total flow volume of approximately 3-5 microliters. Since the microfluidic channel volume is only 0.2 microliters, this mechanism is well suited for cell loading and cell exposures.

The second mechanism is gravity driven perfusion, which is well suited for longer term flows, as this is dependent on the liquid level difference and not the reservoir dimensions. According to specific embodiments of the invention, this may be accomplished by adding more liquid into one reservoir (typically filling near the top of the upper reservoir). The fluidic resistance through the microfluidic channels will determine how long (e.g., 24 hours) to reach equilibrium between the wells and thus determine how often wells should be refilled.

Figure 25:
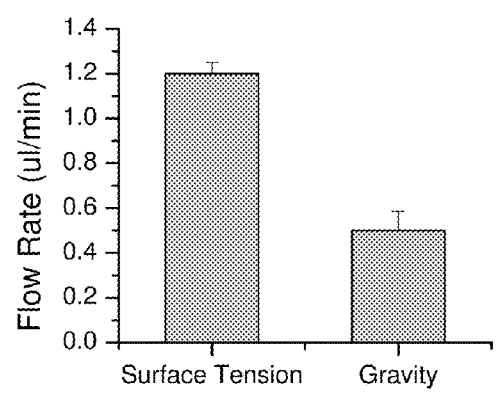
FIG. 25 is a graph illustrating an example of flow rate difference between a surface tension mechanism and a gravity driven mechanism according to specific embodiments of the invention.

FIG. 25 shows the flow rate difference between the surface tension mechanism and the gravity driven mechanism. For the surface tension flow, in an example, 5 microliters was dispensed into the lower reservoir followed by aspiration of the opposing lower reservoir. For the gravity flow, a liquid level difference of 2.5 mm was used, with both wells filled into the upper reservoir portion.

Changing Gravity Flow Rate Via Liquid Level

Figure 26:
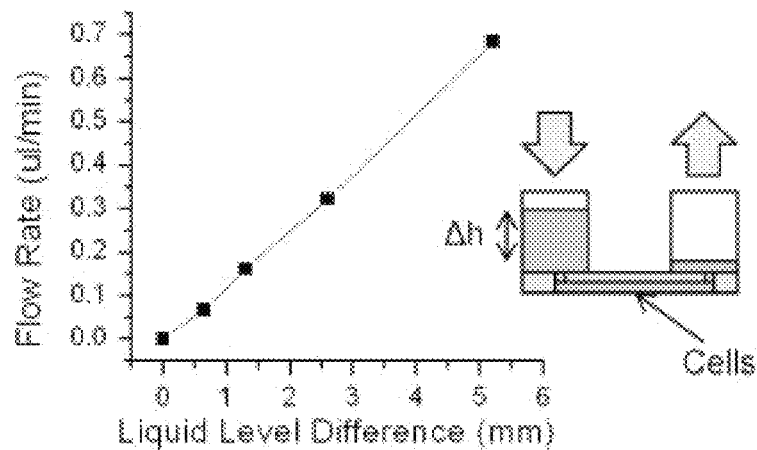
FIG. 26 is a graph illustrating an example of the extent to which gravity perfusion rate is responsive to the liquid level difference between the two upper reservoir wells according to specific embodiments of the invention.

The gravity perfusion rate is also responsive to the liquid level difference between the two upper reservoir wells as illustrated in FIG. 26. This fact allows an automated dispenser/aspirator to control and maintain a given perfusion flow rate over a 10-fold range during culture. Here, different liquid level differences were produced via dispensing volumes and measured for volumetric flow rate.

Controlling Gravity Perfusion Rate Via Plate Tilt Angle

According to specific embodiments of the invention, the liquid height difference between the inlet/outlet wells across the plate can also be precisely controlled using a mechanical tilting platform. In this implementation, it is possible to maintain a constant flow rate over time, as well as back-and-forth flow with different forward and reverse times (i.e. blood flow).

In an example system, perfusion cell culture can be initiated by filling the flow inlet reservoir with 200-300 microliters of fresh medium (e.g., DMEM supplemented with 10% fetal bovine serum) and aspirating the cell inlet upper reservoir. The liquid level difference between the flow inlet and cell inlet wells will then cause a continuous gravity driven flow through the attached cells. For sustained culture, the flow inlet well is refilled and the cell inlet well aspirated during a period depending on fluidic resistance and reservoir volumes (e.g., every 12, 24, 36, 48, 72 hours).

Cell Assay and/or Observation

Cell assay can be performed directly on the microfluidic cell culture using standard optically based reagent kits (e.g. fluorescence, absorbance, luminescence, etc.). For example a cell viability assay utilizing conversion of a substrate to a fluorescent molecule by live cells has been demonstrated (CellTiter Blue reagent by Promega Corporation). The reagent is dispensed into the flow inlet reservoir and exposed to the cells via gravity perfusion over a period of time (e.g., 21 hours). For faster introduction of a reagent or other fluid, the new fluid can be added to the flow inlet reservoir followed by aspiration of the cell inlet reservoir.

Data can be collected directly on the cells/liquid in the microfluidic plate, such as placing the plate into a standard fluorescence plate reader (e.g., Biotek Instruments Synergy 2 model). In some reactions, the substrate may diffuse into the outlet medium, and therefore be easily detected in the cell inlet reservoir. For cell imaging assays, the plate can be placed on a scanning microscope or high content system. For example, an automated Olympus IX71 inverted microscope station can be used to capture viability of cultured liver cells with a 20× objective lens.

By repeatedly filling/aspirating the wells, cells can be maintained for long periods of time with minimal effort (e.g. compared to standard "bioreactors" which require extensive sterile preparation of large fluid reservoirs that cannot be easily swapped out during operation).

9. Automated Systems

Figure 27:
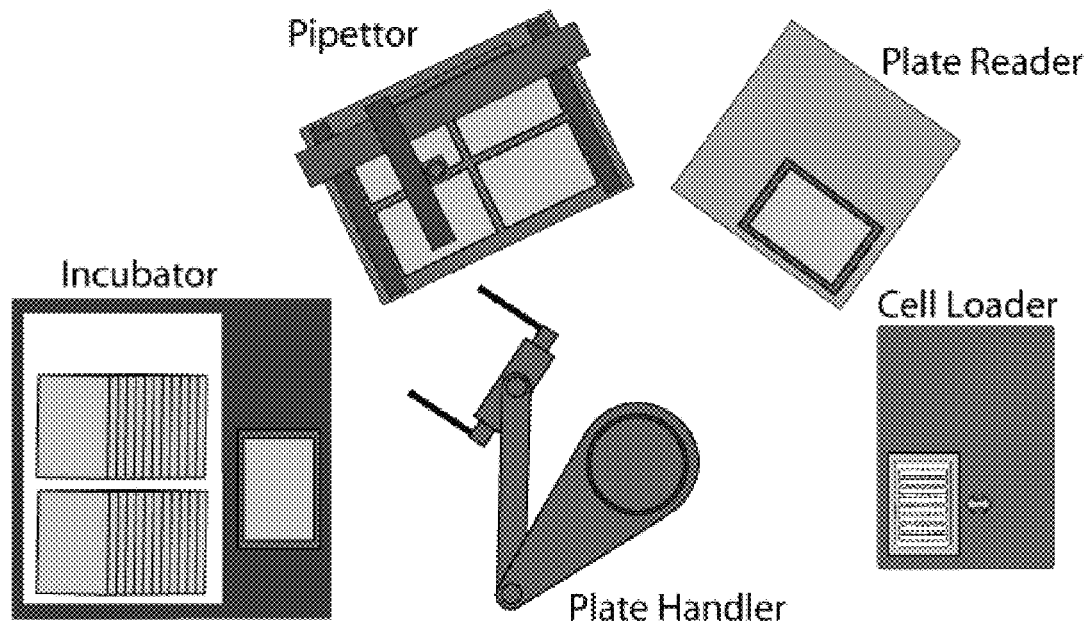
FIG. 27 illustrates a top view schematic of an example cell culture automation system according to specific embodiments of the invention.

FIG. 27 illustrates a top view schematic of an example cell culture automation system according to specific embodiments of the invention. Because the plates are designed to be handled using SBS compliant instruments, various "off-the-shelf" machines can be used to create an automated system. This schematic shows an example of how this is accomplished. A robotic arm (plate handler) moves the microfluidic plates from station to station. An automated incubator stores the plates at the proper temperature and gas environment for long term perfusion via gravity flow. The pipettor dispenses liquids (media, drugs, assay reagents, etc.) to the inlet wells and removes liquid from the outlet wells. A plate reader is used for assay. The cell loader is optionally used to introduce the cells to the microfluidic arrays at the beginning of the experiment. The cell loader in particular is generally not "off-the-shelf" and operates by applying pneumatic pressure to specified wells of the array plate to induce flow. Standard or custom computer software is available to integrate operations.

Figure 28:
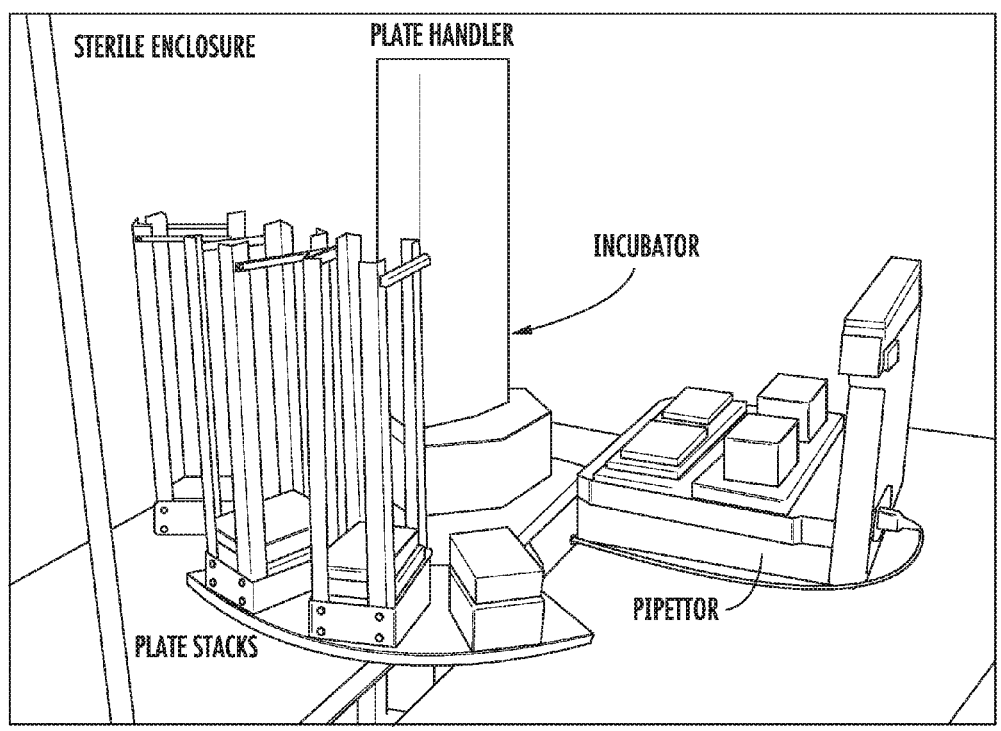
FIG. 28 is a photograph of an example automated microfluidic perfusion array system according to specific embodiments of the invention.

FIG. 28 is a photograph of an example automated microfluidic perfusion array system according to specific embodiments of the invention. The basic process includes: 1) removing the plate from the incubator, 2) removing liquid from the outlet wells via the pipettor, 3) moving a media/drug storage plate from the "plate stacks," 4) transferring liquid from the media/drug plate to the microfluidic plate via the pipettor, 5) placing the microfluidic plate into the incubator, 6) repeat for each plate, 7) repeat after specified time interval (e.g. 24 hours).

Figure 29:
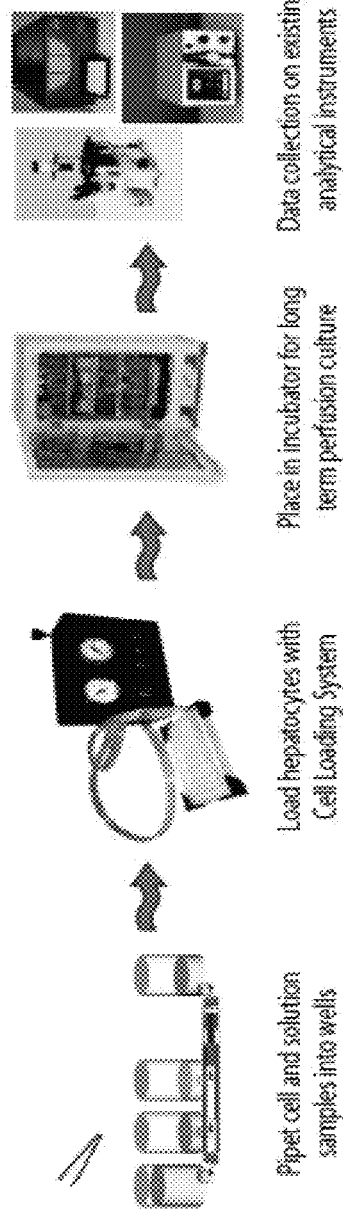
FIG. 29 illustrates operation steps of a less automated or prototype system according to specific embodiments of the invention.
Figure 29:
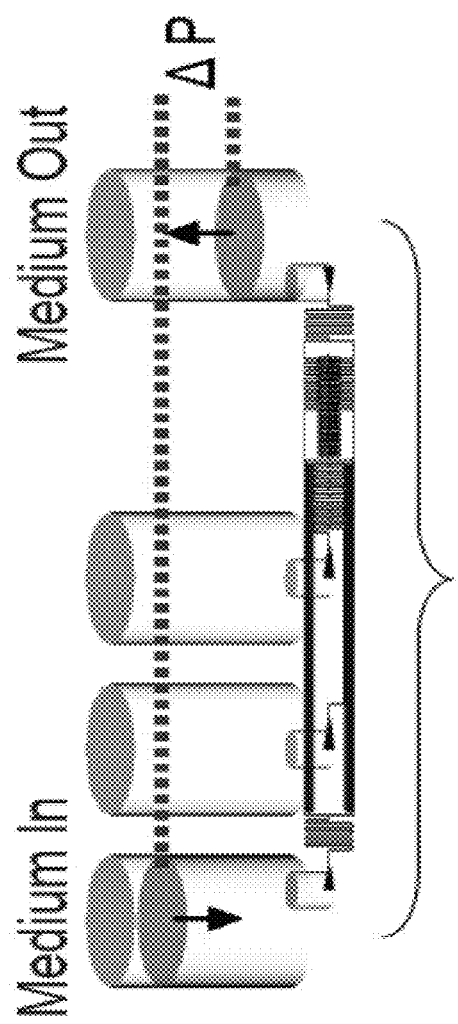

FIG. 29 illustrates operation steps of a less automated or prototype system according to specific embodiments of the invention. The 96-well plate standard allows the microfluidic system to be operated using standard techniques and equipment. For example, liquid dispensing is achieved with standard pipette mechanics, and cell culture and analysis is compatible with existing incubators and plate readers. A custom built cell loading system can be used to load the cells using air pressure as described above. The gravity driven flow culture configuration utilizes the medium level difference between the inlet and outlet well as well as engineering the fluidic resistances to achieve the desirable flow rate in nL/min regime. This provides the significant advantage of being able to "passively" flow culture medium for long periods of time (for example, up to 4 days) without the use of bulky external pumps.

Integrated Systems

Integrated systems for the collection and analysis of cellular and other data as well as for the compilation, storage and access of the databases of the invention, typically include a digital computer with software including an instruction set for sequence searching and/or analysis, and, optionally, one or more of high-throughput sample control software, image analysis software, collected data interpretation software, a robotic control armature for transferring solutions from a source to a destination (such as a detection device) operably linked to the digital computer, an input device (e.g., a computer keyboard) for entering subject data to the digital computer, or to control analysis operations or high throughput sample transfer by the robotic control armature. Optionally, the integrated system further comprises valves, concentration gradients, fluidic multiplexors and/or other microfluidic structures for interfacing to a microchamber as described.

Readily available computational hardware resources using standard operating systems can be employed and modified according to the teachings provided herein, e.g., a PC (Intel x86 or Pentium chip-compatible DOS,™ OS2,™ WINDOWS,™ WINDOWS NT,™ WINDOWS95,™ WINDOWS98,™ LINUX, or even Macintosh, Sun or PCs will suffice) for use in the integrated systems of the invention. Current art in software technology is adequate to allow implementation of the methods taught herein on a computer system. Thus, in specific embodiments, the present invention can comprise a set of logic instructions (either software, or hardware encoded instructions) for performing one or more of the methods as taught herein. For example, software for providing the data and/or statistical analysis can be constructed by one of skill using a standard programming language such as Visual Basic, Fortran, Basic, Java, or the like. Such software can also be constructed utilizing a variety of statistical programming languages, toolkits, or libraries.

FIG. 30 shows an information appliance (or digital device) 700 that may be understood as a logical apparatus that can read instructions from media 717 and/or network port 719, which can optionally be connected to server 720 having fixed media 722. Apparatus 700 can thereafter use those instructions to direct server or client logic, as understood in the art, to embody aspects of the invention. One type of logical apparatus that may embody the invention is a computer system as illustrated in 700, containing CPU 707, optional input devices 709 and 711, disk drives 715 and optional monitor 705. Fixed media 717, or fixed media 722 over port 719, may be used to program such a system and may represent a disk-type optical or magnetic media, magnetic tape, solid state dynamic or static memory, etc. In specific embodiments, the invention may be embodied in whole or in part as software recorded on this fixed media. Communication port 719 may also be used to initially receive instructions that are used to program such a system and may represent any type of communication connection.

Various programming methods and algorithms, including genetic algorithms and neural networks, can be used to perform aspects of the data collection, correlation, and storage functions, as well as other desirable functions, as described herein. In addition, digital or analog systems such as digital or analog computer systems can control a variety of other functions such as the display and/or control of input and output files. Software for performing the electrical analysis methods of the invention are also included in the computer systems of the invention.

Other Embodiments

Although the present invention has been described in terms of various specific embodiments, it is not intended that the invention be limited to these embodiments. Modification within the spirit of the invention will be apparent to those skilled in the art.

It is understood that the examples and embodiments described herein are for illustrative purposes and that various modifications or changes in light thereof will be suggested by the teachings herein to persons skilled in the art and are to be included within the spirit and purview of this application and scope of the claims.

All publications, patents, and patent applications cited herein or filed with this submission, including any references filed as part of an Information Disclosure Statement, are incorporated by reference in their entirety.

What is claimed:

1. A microfluidic structure comprising:
   a culture chamber;
   at least one first object flow outlet disposed on a wall of said culture chamber;
   at least one second object flow outlet disposed on said wall;
   at least one object flow inlet disposed on said wall and between said at least one first object flow outlet and said at least one second object flow outlet for introducing culture objects and object flow media into said culture chamber;
   a flow-around channel allowing fluidic media into said culture chamber, said flow-around channel having a first end in communication with a fluidic media inlet and a second end in communication with a fluidic media outlet, said fluidic media inlet in communication with a first reservoir and said fluidic media outlet in communication with a second reservoir;

said flow-around channel providing fluidic mass transport through a perfusion barrier opposite from said at least one object flow inlet, said at least one first object flow outlet, and said at least one second object flow outlet, wherein said perfusion barrier defines at least two walls of said culture chamber, wherein one wall of said at least two walls defines an opposite wall of said culture chamber, and is configured to prevent cell passage into said flow-around channel;

said perfusion barrier configured to create a low fluidic resistance path within said culture chamber for a flow of cells entering said culture chamber from said at least one object flow inlet, such that said flow of cells encounters a flow of media passing through said perfusion barrier from said flow-around channel, causing at least part of said flow of cells to take an approximately 180 degree turn and exit said culture chamber via said at least one first object flow outlet and said at least one second object flow outlet.

2. The structure of claim 1 further comprising:
at least one separate air diffusion channel adjacent to the culture chamber and running along most of one side of the culture chamber.

3. The structure of claim 1 further comprising:
a second object flow inlet adjacent to the at least one object flow inlet providing a split object loading inlet.

4. The structure of claim 1 further wherein:
the perfusion barrier is configured to prevent a gel from filling said flow-around channel.

5. The structure of claim 4 further comprising:
the flow-around channel comprising more than one half of the culture chamber.

6. The structure of claim 1 further wherein the shape of the culture chamber is selected from the group consisting of:
a rectangle;
a rectangle with one or more rounded edges;
a circle; and
a culture chamber with at least one side that is an elliptical or circular shape.

7. The structure of claim 1 further wherein:
said at least one object flow inlet is configured to load and hold objects embedded in a 3D gel or matrix and said perfusion barrier is configured to provide fluid flow while preventing flow of clogging by the 3D gel or matrix.

8. The structure of claim 1 further comprising:
wherein the flow of cells is loaded via capillary force from said at least one object flow inlet and out from the at least one first object flow outlet and the at least one second object flow outlet away from the at least one object flow inlet; and wherein a very small amount of flow exits the culture chamber from the at least one first object flow outlet and the at least one second object flow outlet, thereby tending to distribute cells more evenly in the culture chamber.

9. The structure of claim 1 wherein:
the culture chamber is between about 0.1 millimeters and about 5 millimeters high;
the flow-around channel is between about 10 microns and 100 microns high, with a cross section of between about 50 square microns and about 10,000 square microns;
the perfusion barrier provides a perfusion passage between about 1 microns high and about 10 microns high, with a cross section of between about 1 square microns and about 100 square microns.

10. The structure of claim 1 further wherein:
the culture chamber further comprises a glass floor and is configured to perform the culture of cells in 2D culture using liquid culture medium or 3D culture using a gel medium,
wherein in 2D culture, cells adhere to said glass floor due to a low culture flow rate from the at least one object flow inlet to the at least one first object flow outlet and the at least one second object flow outlet; and
wherein in 3D culture, cells are embedded in a gel and dispensed into the culture chamber with the gel localized to the culture chamber by the perfusion barrier, allowing medium to flow around the gel/perfusion barrier and diffuse in to feed the cells.

11. The structure of claim 1 further comprising a serpentine channel disposed between said first reservoir and said flow-around channel, wherein said serpentine channel has a fluidic resistance, and said fluidic resistance determines said flow rate of said fluid in said flow-around channel.

12. The structure of claim 1 further comprising a serpentine channel disposed between said flow-around channel and said second reservoir, wherein said serpentine channel has a fluidic resistance, and said fluidic resistance determines said flow rate of said fluid in said flow-around channel.

13. The structure of claim 1, wherein a flow rate of said fluid through said flow-around channel is determined based on a difference in fluid level between said first reservoir and said second reservoir.

14. The structure of claim 1, wherein said perfusion barrier defines three walls of said culture chamber.

15. The structure of claim 1, wherein said perfusion barrier encloses said culture chamber.

16. The structure of claim 1, wherein said perfusion barrier comprises a non-linear structure.

* * * * *